US006811783B1

(12) United States Patent
Murdin et al.

(10) Patent No.: US 6,811,783 B1
(45) Date of Patent: Nov. 2, 2004

(54) IMMUNOGENIC COMPOSITIONS FOR PROTECTION AGAINST CHLAMYDIAL INFECTION

(75) Inventors: Andrew D. Murdin, Newmarket (CA); Pamela L. Dunn, Mississauga (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/391,606

(22) Filed: Sep. 7, 1999

(51) Int. Cl.$^7$ ........................ A61K 39/02; A61K 39/00; C07K 1/00; C07H 21/04
(52) U.S. Cl. ............................... 424/190.1; 424/185.1; 530/350; 536/23.7
(58) Field of Search ........................... 424/185.1, 190.1; 530/350, 300; 536/23.7, 23.1, 23.5; 514/44

(56) References Cited

U.S. PATENT DOCUMENTS

| | | | |
|---|---|---|---|
| 4,245,050 A | 1/1981 | Nakanishi et al. | ........... 435/191 |
| 5,015,580 A | 5/1991 | Christou et al. | ............ 800/267 |
| 5,075,109 A | 12/1991 | Tice et al. | ................ 424/193.1 |
| 5,151,264 A | 9/1992 | Samain et al. | ............. 424/1.21 |

FOREIGN PATENT DOCUMENTS

| WO | WO 91/06282 | 5/1991 |
|---|---|---|
| WO | WO 93/24640 | 12/1993 |
| WO | WO 94/24263 | 10/1994 |
| WO | WO 94/27435 | 12/1994 |
| WO | WO 95/34308 | 12/1995 |
| WO | WO 98/02546 | 1/1998 |
| WO | WO-98/02546 | * 6/1998 |

OTHER PUBLICATIONS

Eck et al.; Gene–Based Therapy, 1996, The Pharamacological Basis of Therapeutics: 77–101.*
Rudinger; Characteristics of the amino acids as components of a peptide hormone sequence, 1976, Peptide Hormones: 1–7.*
Kaye et. al.; A single amino acid substitution results in a retinoblastoma protein defective in phosphorylation and oncoprotein binding, 1990, Proc. Natl. Acad. Sci.: 6922–6926.*
Stagg, Vaccines against Chlamydia: approaches and progress, 1998, Molecular Medicine Today, pp. 166–173.*
Anderson, Human gene therapy, 1998, NATURE, vol. 392, pp. 25–30.*
McCluskie et al., Route and method of delivery of DNA vaccine influence immune responses in mice and non–human primates, 1999, Molecular Medicine, pp. 287–300.*
Melgosa et al., Isolation and characterization of a gene encoding a Chlamydia pneumoniae 76–kilodation protein containing a species–specific epitope, 1994, Infection and Immunity, pp. 880–886.*
Grayston et al. (1995), Journal of Infectious Diseases 168:1231–1235.

Campos et al. (1995), Investigation of Ophthalmology and Visual Science 36:1477–1491.
Grayston et al (1990), Journal of Infectious Diseases 161:618–625.
Marrie (1993), Clinical Infectious Diseases. 18:501–515.
Wang et al (1986), Chlamydial infections. Cambridge University Press, Cambridge. p. 329–333.
Normann et al (1998), Acta Paediatrica, 87:23–27.
Saikku et al. (1988), Lancet 983–985.
Thom et al. (1992), JAMA 268:68–72.
Linnanmaki et al. (1993), Circulation 87:1130–1134.
Saikku et al. (1992), Annals Internal Medicine 116:273–278.
Melnick et al (1993), American Journal of Medicine 95:499–504.
Shor et al. (1992), South African Medical Journal 82:158–161.
Kuo et al. (1993), Journal of Infectious Diseases 167:841–849.
Kuo et al. (1993), Arteriosclerosis and Thrombosis 13:1501–1504.
Campbell et al (1995), Journal of Infectious Diseases 172:585–588.
Chiu et al. Circulation, Oct. 7, 1997; 96(7);2144–2148.
Ramirez et al (1996) Annals of Internal Medicine 125:979–982.
Jackson et al. Abst. K121, p272, 36th ICAAC, Sept. 15–18, 1996, New Orleans.
Fong et al (1997) Journal of Clinical Microbiology 35:48–52.
Hahn DL, et al. Evidence for *Chlamydia pneumoniae* infection in steroid–dependent asthma. Ann Allergy Asthma Immunol. Jan. 1998; 80(1): 45–49.
Hahn DL, et al. Association of *Chlamydia pneumoniae* Iga antibodies with recently symptomatic asthma. Epidemiol Infect. Dec. 1996; 117(3) : 513–517.
Bjornsson E, et al. Serology of chlamydia in relation to asthma and bronchial hyperresponsiveness. Scand J Infect Dis. 1996; 28(1): 63–69.

(List continued on next page.)

*Primary Examiner*—Shin-Lin Chen
(74) *Attorney, Agent, or Firm*—Sim & McBurney

(57) ABSTRACT

A protective immune response against Chlamydial infection is achieved by in vivo administration of an immunogenic composition comprising two vectors and a pharmaceutically-acceptable carrier therefor. One of the vectors comprises a first nucleotide sequence encoding a major outer membrane protein (MOMP) of a strain of Chlamydia, preferably *C. pneumoniae*, and a promoter sequence operatively coupled to the first nucleotide sequence for expression of the MOMP in the host. The other of the vectors comprises a second nucleotide sequence encoding a 76 kDa protein of a strain of Chlamydia, preferably *C. pneumoniae*, and a promoter sequence operatively coupled to the second nucleotide sequence for expression of the 76 kDa protein in the host. The protection efficiency which is achieved by the immunization procedure is enhanced over that attained with the individual vectors alone.

8 Claims, 10 Drawing Sheets-

OTHER PUBLICATIONS

Hahn DL. Treatment of *Chlamydia pneumoniae* infection in adult asthma: a before–after trial. J Fam Pract. Oct. 1995; 41(4): 345–351.

Allegra L, et al. Acute exacerbations of asthma in adults: role of *Chlamydia pneumoniae* infection. Eur Respir J. Dec. 1994; 7(12): 2165–2168.

Hahn DL, et al. Association of *Chlamydia pneumoniae* (strain TWAR) infection with wheezing, asthmatic bronchitis, and adult–onset asthma. JAMA. Jul. 10, 1991; 266(2): 225–230.

Pal et al. (1996) Infection and Immunity.64:5341.

Jones et al. (1995) Vaccine 13:715–723.

Igietsemes et al. (1993) Immunology 5:317.

Igietseme et al (1993) Regional Immunology 5:317–324.

Magee et al (1993) Regional Immunology 5: 305–311.

Landers et al (1991) Infection & Immunity 59:3774–3777.

Magee et al (1995) Infection & Immunity 63:516–521.

Cotter et al. (1995) Infection and Immunity 63:4704–4714.

Campbell et al (1990) Infection and Immunity 58:93–97.

McCafferty et al (1995) Infection & Immunity 63:2387–2389.

Knudsen et al (1996)Third Meeting of the European Society for Chlamydia Research, Vienna.

Wiedmann–Al–Ahmad M, et al. Reactions of polyclonal and neutralizing anti–p54 monoclonal antibodies with an isloated, species–specific 54–kilodalton protein of *Chlamydia pneumoniae*. Clin Diagn Lab Immunol. Nov. 1997; 4(6): 700–704.

Xiang, 1995, Immunity 2: 129–135.

Tang et al, Nature 1992, 356:152–154.

Davis et al., Vaccine 1994, 12:1503–1509.

Yang et al, 1993, Infection & Immunity, vol. 61, pp. 2037–2040.

Chi E.Y., Kuo C.C., Grayston J.T. 1987. Unique ultrastructure in the elementary body of Chlamydia sp strain TWAR. J. Bacteriol 169(8):3757–3763.

\* cited by examiner

Figure 1 Nucleotide Sequence of the 76kDa *C. pneumoniae* gene

CDS 5'
(175)..(825)
CDS 3'
(940)..(2409)

```
ttgcggtgct gttaacggtg gagggcagtg tagtctgagc agtactcgtt gctgccgcgc   60
gcgccaccag acataatagc tgacagacta acagactgtt cctttccatg ggtcttttct  120
gcagtcaccg tcgtcgacac gtgtgatcag atatcgcggc cgctctagac cgcc atg    177
                                                              Met
                                                               1 aca aaa aaa cat tat gct tgg gtt gta gaa ggg att ctc aat cgt ttg    225
Thr Lys Lys His Tyr Ala Trp Val Val Glu Gly Ile Leu Asn Arg Leu
         5                  10                  15 cct aaa cag ttt ttt gtg aaa tgt agt gtt gtc gac tgg aac aca ttc    273
Pro Lys Gln Phe Phe Val Lys Cys Ser Val Val Asp Trp Asn Thr Phe
         20                  25                  30 gtt cct tca gaa acc tcc act aca gaa aaa gct gct aca aac gct atg    321
Val Pro Ser Glu Thr Ser Thr Thr Glu Lys Ala Ala Thr Asn Ala Met
         35                  40                  45 aaa tac aaa tac tgt gtt tgg cag tgg ctc gtc gga aag cat agt cag    369
Lys Tyr Lys Tyr Cys Val Trp Gln Trp Leu Val Gly Lys His Ser Gln
 50                  55                  60                  65 gtt cct tgg atc aat gga cag aaa aag cct cta tat ctt tat gga gct    417
Val Pro Trp Ile Asn Gly Gln Lys Lys Pro Leu Tyr Leu Tyr Gly Ala
             70                  75                  80 ttc tta atg aac cct tta gca aag gct acg aag act acg tta aat gga    465
Phe Leu Met Asn Pro Leu Ala Lys Ala Thr Lys Thr Thr Leu Asn Gly
         85                  90                  95 aaa gaa aac cta gct tgg ttt att gga gga act tta ggg gga ctc aga    513
Lys Glu Asn Leu Ala Trp Phe Ile Gly Gly Thr Leu Gly Gly Leu Arg
         100                 105                 110 aaa gct gga gac tgg tct gcc aca gta cgt tat gag tat gtc gaa gcc    561
Lys Ala Gly Asp Trp Ser Ala Thr Val Arg Tyr Glu Tyr Val Glu Ala
         115                 120                 125 ttg tca gtt cca gaa ata gat gtt tca ggg att ggc cgt ggt aat tta    609
Leu Ser Val Pro Glu Ile Asp Val Ser Gly Ile Gly Arg Gly Asn Leu
 130                 135                 140                 145 tta aag ttt tgg ttc gcc caa gca att gct gct aac tat gat cct aaa    657
Leu Lys Phe Trp Phe Ala Gln Ala Ile Ala Ala Asn Tyr Asp Pro Lys
```

```
                         150                      155                      160
    gag gct aat agt ttt aca aat tat aaa gga ttt tcc gct cta tat atg    705
    Glu Ala Asn Ser Phe Thr Asn Tyr Lys Gly Phe Ser Ala Leu Tyr Met
                165                  170                  175 tat ggc atc aca gat tct cta tca ttc aga gct tat ggg gct tac tcc    753
    Tyr Gly Ile Thr Asp Ser Leu Ser Phe Arg Ala Tyr Gly Ala Tyr Ser
                180                  185                  190 aaa cca gca aac gat aaa ctc ggc agt gat ttt act ttc cga aag ttt    801
    Lys Pro Ala Asn Asp Lys Leu Gly Ser Asp Phe Thr Phe Arg Lys Phe
                195                  200                  205 gat cta ggt ata att tca gcg ttt taagtcaaat tttaataaaa tctttaaaaa   855
    Asp Leu Gly Ile Ile Ser Ala Phe
    210                 215 caggctcgca ttaattatta gtgagagctt ttttttatt ttttataata aaactaaaag   915
atttttatta tttttgagt tttt atg gtt aat cct att ggt cca ggt cct      966
                             Met Val Asn Pro Ile Gly Pro Gly Pro
                                             220                  225 ata gac gaa aca gaa cgc aca cct ccc gca gat ctt tct gct caa gga   1014
    Ile Asp Glu Thr Glu Arg Thr Pro Pro Ala Asp Leu Ser Ala Gln Gly
                230                  235                  240 ttg gag gcg agt gca gca aat aag agt gcg gaa gct caa aga ata gca   1062
    Leu Glu Ala Ser Ala Ala Asn Lys Ser Ala Glu Ala Gln Arg Ile Ala
                245                  250                  255 ggt gcg gaa gct aag cct aaa gaa tct aag acc gat tct gta gag cga   1110
    Gly Ala Glu Ala Lys Pro Lys Glu Ser Lys Thr Asp Ser Val Glu Arg
                260                  265                  270 tgg agc atc ttg cgt tct gca gtg aat gct ctc atg agt ctg gca gat   1158
    Trp Ser Ile Leu Arg Ser Ala Val Asn Ala Leu Met Ser Leu Ala Asp
    275                 280                  285                  290 aag ctg ggt att gct tct agt aac agc tcg tct tct act agc aga tct   1206
    Lys Leu Gly Ile Ala Ser Ser Asn Ser Ser Ser Ser Thr Ser Arg Ser
                295                  300                  305 gca gac gtg gac tca acg aca gcg acc gca cct acg cct cct cca ccc   1254
    Ala Asp Val Asp Ser Thr Thr Ala Thr Ala Pro Thr Pro Pro Pro Pro
                310                  315                  320 acg tct gat gat tat aag act caa gcg caa aca gct tac gat act atc   1302
    Thr Ser Asp Asp Tyr Lys Thr Gln Ala Gln Thr Ala Tyr Asp Thr Ile
                325                  330                  335 ttt acc tca aca tca cta gct gac ata cag gct gct ttg gtg agc ctc   1350
    Phe Thr Ser Thr Ser Leu Ala Asp Ile Gln Ala Ala Leu Val Ser Leu
```

```
           340                    345                      350 cag gat gct gtc act aat ata aag gat aca gcg gct act gat gag gaa    1398
    Gln Asp Ala Val Thr Asn Ile Lys Asp Thr Ala Ala Thr Asp Glu Glu
    355                 360                 365                 370 acc gca atc gct gcg gag tgg gaa act aag aat gcc gat gca att aaa    1446
    Thr Ala Ile Ala Ala Glu Trp Glu Thr Lys Asn Ala Asp Ala Ile Lys
                        375                 380                 385 gtt ggc gcg caa att aca gaa tta gcg aaa tat gct tcg gat aac caa    1494
    Val Gly Ala Gln Ile Thr Glu Leu Ala Lys Tyr Ala Ser Asp Asn Gln
                    390                 395                 400 gcg att ctt gac tct tta ggt aaa ctg act tcc ttc gac ctc tta cag    1542
    Ala Ile Leu Asp Ser Leu Gly Lys Leu Thr Ser Phe Asp Leu Leu Gln
                    405                 410                 415 act gct ctt ctc caa tct gta gca aac aat aac aaa gca gct gag ctt    1590
    Thr Ala Leu Leu Gln Ser Val Ala Asn Asn Asn Lys Ala Ala Glu Leu
            420                 425                 430 ctt aaa gag atg caa gat aac cca gta gtc cca ggg aaa acg cct gca    1638
    Leu Lys Glu Met Gln Asp Asn Pro Val Val Pro Gly Lys Thr Pro Ala
    435                 440                 445                 450 att gct caa tct tta gtt gat cag aca gat gct aca gcg aca cag ata    1686
    Ile Ala Gln Ser Leu Val Asp Gln Thr Asp Ala Thr Ala Thr Gln Ile
                        455                 460                 465 gag aaa gat gga aat gcg att ggg gat gca tat ttt gca gga cag aac    1734
    Glu Lys Asp Gly Asn Ala Ile Gly Asp Ala Tyr Phe Ala Gly Gln Asn
                    470                 475                 480 gct agt gga gct gta gaa aat gct aaa tct aat aac agt ata agc aac    1782
    Ala Ser Gly Ala Val Glu Asn Ala Lys Ser Asn Asn Ser Ile Ser Asn
            485                 490                 495 ata gat tca gct aaa gca gca atc gct act gct aag aca caa ata gct    1830
    Ile Asp Ser Ala Lys Ala Ala Ile Ala Thr Ala Lys Thr Gln Ile Ala
    500                 505                 510 gaa gct cag aaa aag ttc ccc gac tct cca att ctt caa gaa gcg gaa    1878
    Glu Ala Gln Lys Lys Phe Pro Asp Ser Pro Ile Leu Gln Glu Ala Glu
    515                 520                 525                 530 caa atg gta ata cag gct gag aaa gat ctt aaa aat atc aaa cct gca    1926
    Gln Met Val Ile Gln Ala Glu Lys Asp Leu Lys Asn Ile Lys Pro Ala
                    535                 540                 545 gat ggt tct gat gtt cca aat cca gga act aca gtt gga ggc tcc aag    1974
    Asp Gly Ser Asp Val Pro Asn Pro Gly Thr Thr Val Gly Gly Ser Lys
            550                 555                 560
```

```
caa caa gga agt agt att ggt agt att cgt gtt tcc atg ctg tta gat    2022
Gln Gln Gly Ser Ser Ile Gly Ser Ile Arg Val Ser Met Leu Leu Asp
        565             570             575 gat gct gaa aat gag acc gct tcc att ttg atg tct ggg ttt cgt cag    2070
Asp Ala Glu Asn Glu Thr Ala Ser Ile Leu Met Ser Gly Phe Arg Gln
580             585             590 atg att cac atg ttc aat acg gaa aat cct gat tct caa gct gcc caa    2118
Met Ile His Met Phe Asn Thr Glu Asn Pro Asp Ser Gln Ala Ala Gln
595             600             605             610 cag gag ctc gca gca caa gct aga gca gcg aaa gcc gct gga gat gac    2166
Gln Glu Leu Ala Ala Gln Ala Arg Ala Ala Lys Ala Ala Gly Asp Asp
            615             620             625 agt gct gct gca gcg ctg gca gat gct cag aaa gct tta gaa gcg gct    2214
Ser Ala Ala Ala Ala Leu Ala Asp Ala Gln Lys Ala Leu Glu Ala Ala
            630             635             640 cta ggt aaa gct ggg caa caa cag ggc ata ctc aat gct ttg gga cag    2262
Leu Gly Lys Ala Gly Gln Gln Gln Gly Ile Leu Asn Ala Leu Gly Gln
        645             650             655 atc gct tct gct gct gtt gtg agc gca gga gtc ctc ccg ctg cag caa    2310
Ile Ala Ser Ala Ala Val Val Ser Ala Gly Val Leu Pro Leu Gln Gln
        660             665             670 gtt cta tgg atc cga gct cgg tac caa gct tac gta gaa caa aaa ctc    2358
Val Leu Trp Ile Arg Ala Arg Tyr Gln Ala Tyr Val Glu Gln Lys Leu
675             680             685     myc     690 atc tca gaa gag gat ctg aat agc gcc gtc gac cat cat cat cat cat    2406
Ile Ser Glu Glu Asp Leu Asn Ser Ala Val Asp His His His His His
            695             700             His 705 cat tgagtttaaa cggtctccag cttaagttta aaccgctgat cagcctcgac         2459
His tgtgccttct agttgccagc catctgttgt ttgcccctcc cccgtgcctt ccttgaccct  2519
ggaaggtgcc actcccactg tcctt                                        2545
```

Figure 2 Construction of pCAD76kDa
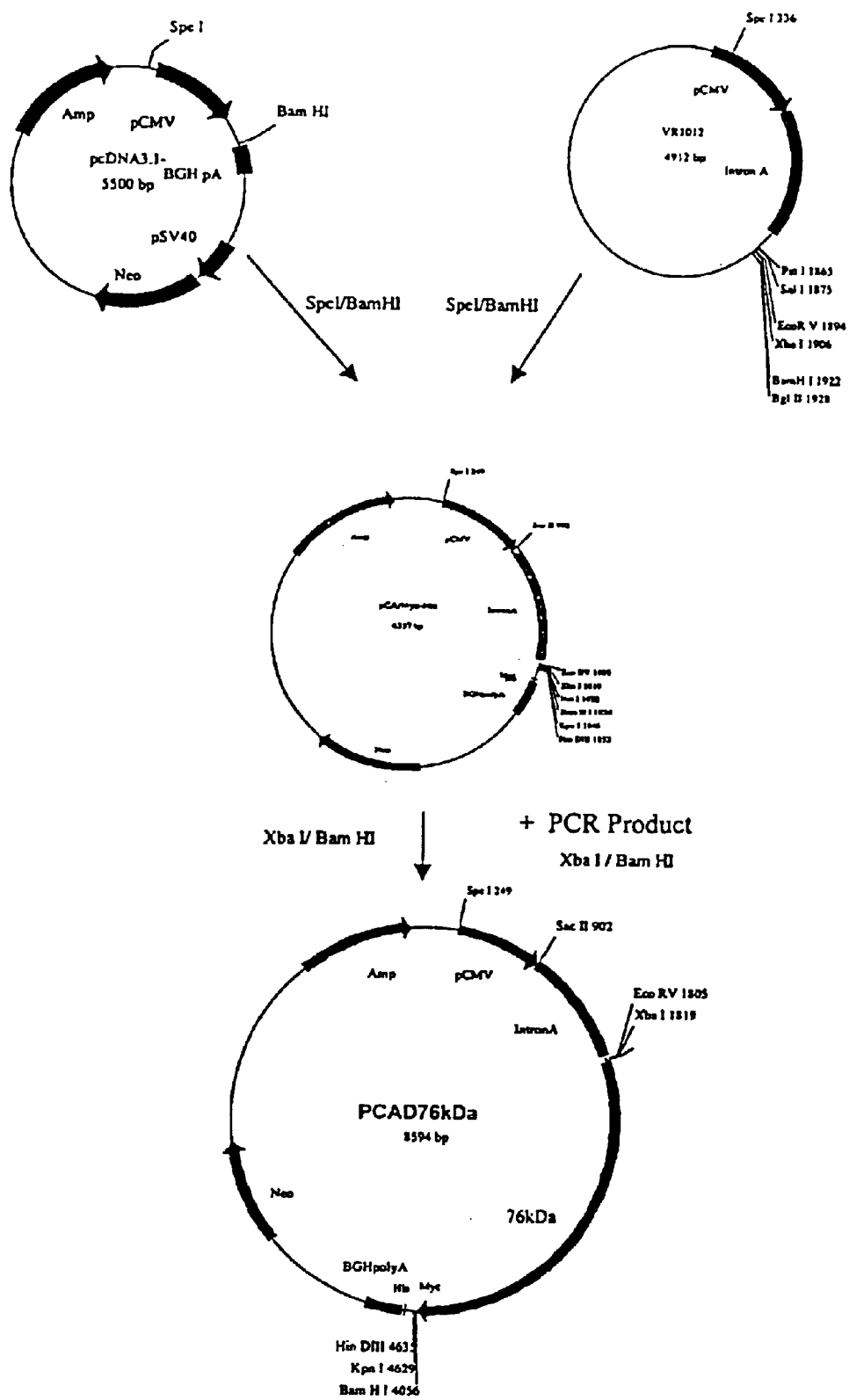

Figure 3 Nucleotide sequence of the *C. pneumoniae* MOMP gene.

(126)..(1307)

```
tgagcagtac tcgttgctgc cgcgcgcgcc accagacata atagctgaca gactaacaga   60
ctgttccttt ccatgggtct tttctgcagt caccgtcgtc gacacgtgtg atcagatatc  120 ccacc atg ttg cct gta ggg aac cct tct gat cca agc tta tta att gat  170
      Met Leu Pro Val Gly Asn Pro Ser Asp Pro Ser Leu Leu Ile Asp
       1               5                  10                   15 ggt aca ata tgg gaa ggt gct gca gga gat cct tgc gat cct tgc gct   218
Gly Thr Ile Trp Glu Gly Ala Ala Gly Asp Pro Cys Asp Pro Cys Ala
                 20                  25                  30 act tgg tgc gac gct att agc tta cgt gct gga ttt tac gga gac tat   266
Thr Trp Cys Asp Ala Ile Ser Leu Arg Ala Gly Phe Tyr Gly Asp Tyr
            35                  40                  45 gtt ttc gac cgt atc tta aaa gta gat gca cct aaa aca ttt tct atg   314
Val Phe Asp Arg Ile Leu Lys Val Asp Ala Pro Lys Thr Phe Ser Met
        50                  55                  60 gga gcc aag cct act gga tcc gct gct gca aac tat act act gcc gta   362
Gly Ala Lys Pro Thr Gly Ser Ala Ala Ala Asn Tyr Thr Thr Ala Val
    65                  70                  75 gat aga cct aac ccg gcc tac aat aag cat tta cac gat gca gag tgg   410
Asp Arg Pro Asn Pro Ala Tyr Asn Lys His Leu His Asp Ala Glu Trp
80                  85                  90                  95 ttc act aat gca ggc ttc att gcc tta aac att tgg gat cgc ttt gat   458
Phe Thr Asn Ala Gly Phe Ile Ala Leu Asn Ile Trp Asp Arg Phe Asp
                    100                 105                 110 gtt ttc tgt act tta gga gct tct aat ggt tac att aga gga aac tct   506
Val Phe Cys Thr Leu Gly Ala Ser Asn Gly Tyr Ile Arg Gly Asn Ser
                115                 120                 125 aca gcg ttc aat ctc gtt ggt tta ttc gga gtt aaa ggt act act gta   554
Thr Ala Phe Asn Leu Val Gly Leu Phe Gly Val Lys Gly Thr Thr Val
            130                 135                 140 aat gca aat gaa cta cca aac gtt tct tta agt aac gga gtt gtt gaa   602
Asn Ala Asn Glu Leu Pro Asn Val Ser Leu Ser Asn Gly Val Val Glu
        145                 150                 155 ctt tac aca gac acc tct ttc tct tgg agc gta ggc gct cgt gga gcc   650
Leu Tyr Thr Asp Thr Ser Phe Ser Trp Ser Val Gly Ala Arg Gly Ala
160                 165                 170                 175
```

```
tta tgg gaa tgc ggt tgt gca act ttg gga gct gaa ttc caa tat gca   698
Leu Trp Glu Cys Gly Cys Ala Thr Leu Gly Ala Glu Phe Gln Tyr Ala
            180             185                 190 cag tcc aaa cct aaa gtt gaa gaa ctt aat gtg atc tgt aac gta tcg   746
Gln Ser Lys Pro Lys Val Glu Glu Leu Asn Val Ile Cys Asn Val Ser
            195             200                 205 caa ttc tct gta aac aaa ccc aag ggc tat aaa ggc gtt gct ttc ccc   794
Gln Phe Ser Val Asn Lys Pro Lys Gly Tyr Lys Gly Val Ala Phe Pro
            210             215                 220 ttg cca aca gac gct ggc gta gca aca gct act gga aca aag tct gcg   842
Leu Pro Thr Asp Ala Gly Val Ala Thr Ala Thr Gly Thr Lys Ser Ala
    225             230                 235 acc atc aat tat cat gaa tgg caa gta gga gcc tct cta tct tac aga   890
Thr Ile Asn Tyr His Glu Trp Gln Val Gly Ala Ser Leu Ser Tyr Arg
240             245                 250                 255 cta aac tct tta gtg cca tac att gga gta caa tgg tct cga gca act   938
Leu Asn Ser Leu Val Pro Tyr Ile Gly Val Gln Trp Ser Arg Ala Thr
            260             265                 270 ttt gat gct gat aac atc cgc att gct cag cca aaa cta cct aca gct   986
Phe Asp Ala Asp Asn Ile Arg Ile Ala Gln Pro Lys Leu Pro Thr Ala
            275             280                 285 gtt tta aac tta act gca tgg aac cct tct tta cta gga aat gcc aca  1034
Val Leu Asn Leu Thr Ala Trp Asn Pro Ser Leu Leu Gly Asn Ala Thr
    290             295                 300 gca ttg tct act act gat tcg ttc tca gac ttc atg caa att gtt tcc  1082
Ala Leu Ser Thr Thr Asp Ser Phe Ser Asp Phe Met Gln Ile Val Ser
305             310                 315 tgt cag atc aac aag ttt aaa tct aga aaa gct tgt gga gtt act gta  1130
Cys Gln Ile Asn Lys Phe Lys Ser Arg Lys Ala Cys Gly Val Thr Val
320             325                 330                 335 gga gct act tta gtt gat gct gat aaa tgg tca ctt act gca gaa gct  1178
Gly Ala Thr Leu Val Asp Ala Asp Lys Trp Ser Leu Thr Ala Glu Ala
            340             345                 350 cgt tta att aac gag aga gct gct cac gta tct ggt cag ttc aga ttc  1226
Arg Leu Ile Asn Glu Arg Ala Ala His Val Ser Gly Gln Phe Arg Phe
            355             360                 365 cgg tac caa gct tac gta gaa caa aaa ctc atc tca gaa gag gat ctg  1274
Arg Tyr Gln Ala Tyr Val Glu Gln Lys Leu Ile Ser Glu Glu Asp Leu
            370             375                 380 aat agc gcc gtc gac cat cat cat cat cat cat tgagtttaaa cggtctccag 1327
Asn Ser Ala Val Asp His His His His His His
```

```
           385                 390
cttaagttta aaccgctgat cagcctcgac tgtgccttct agttgccagc catctgttgt 1387 ttgcccctcc cccgtgcctt ccttgaccct ggaaggtgc                        1426
```

Figure 4 Construction of pCAMOMP
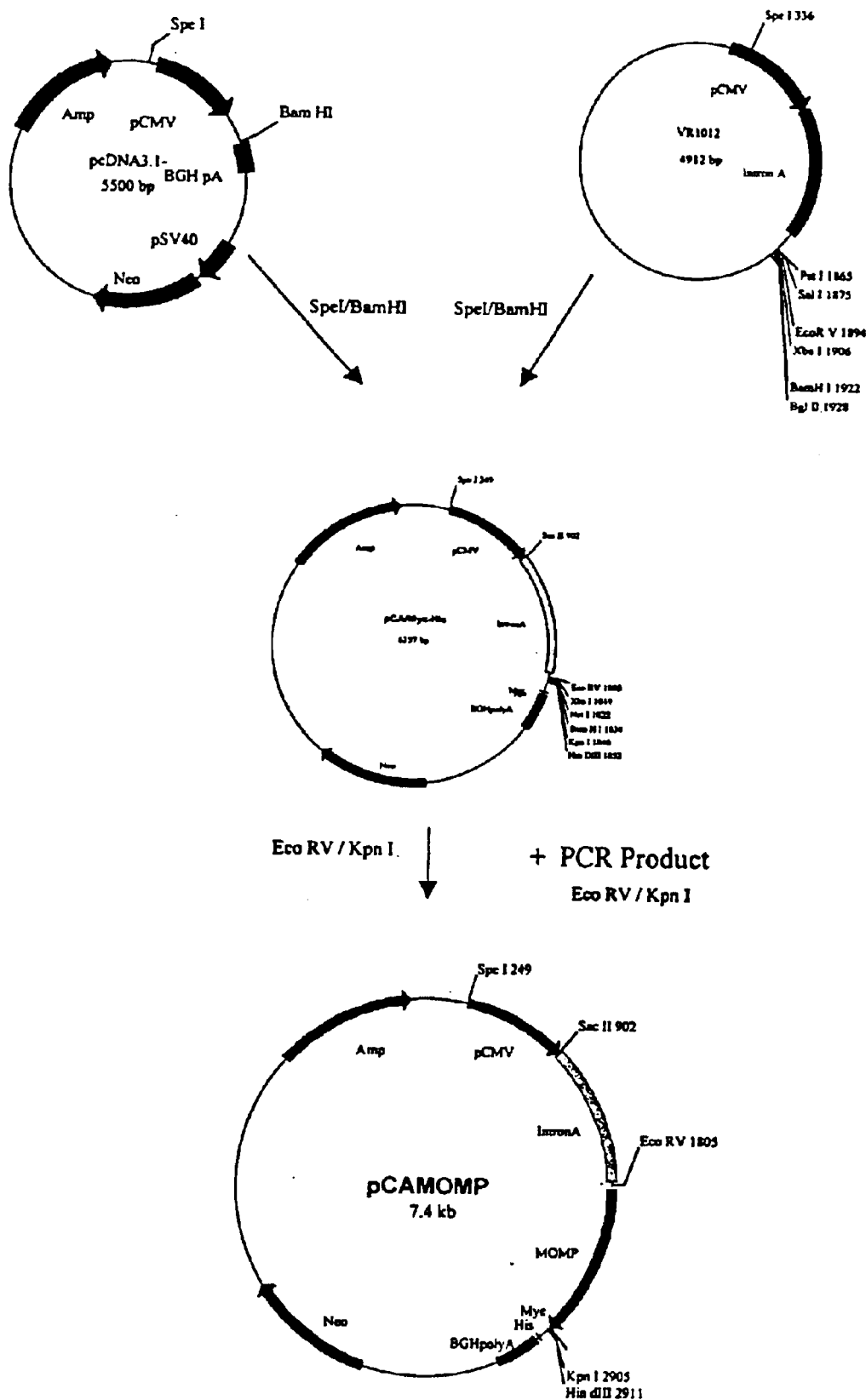

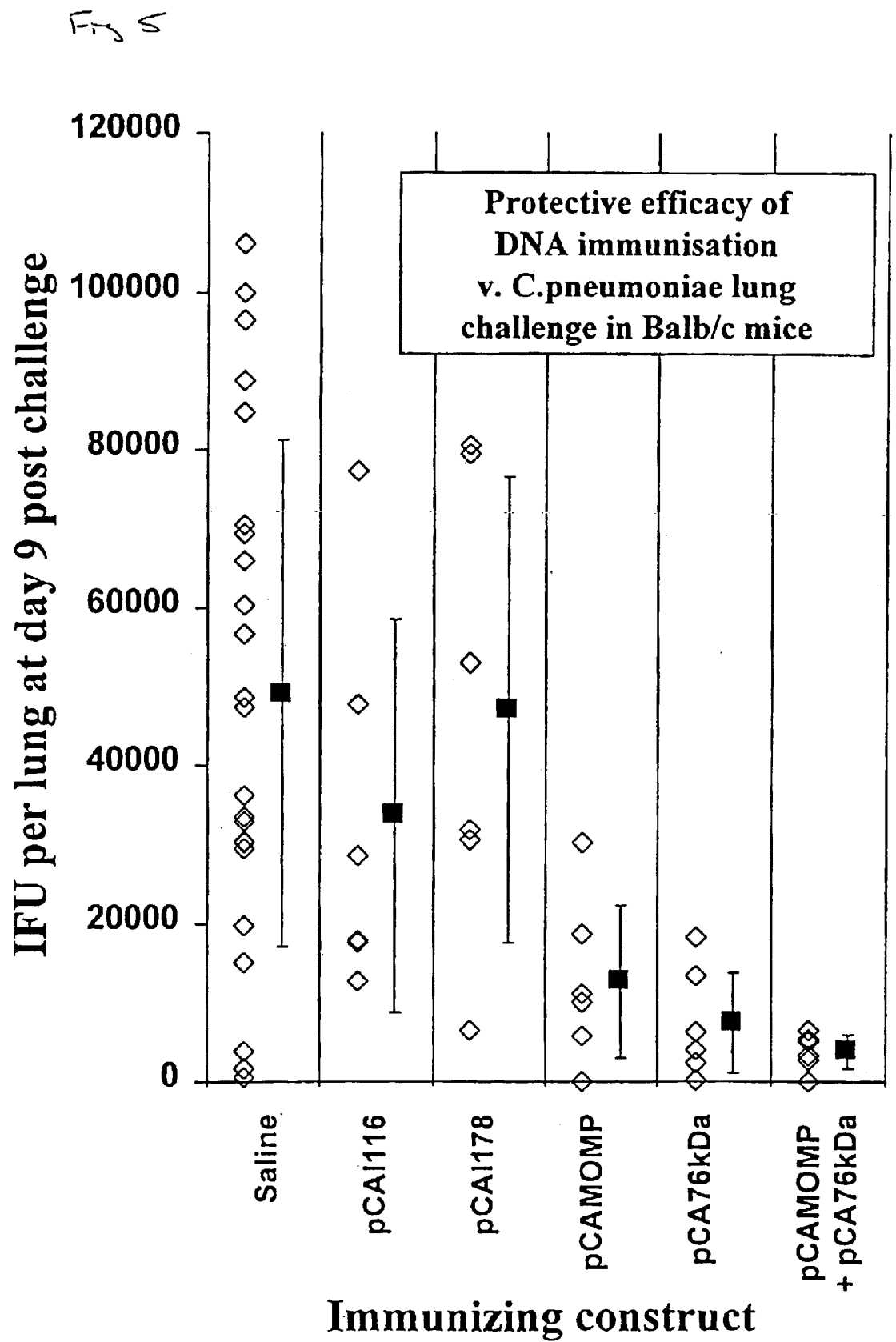

SEQUENCE LISTING

<160> NUMBER OF SEQ ID NOS: 20

<210> SEQ ID NO 1
<211> LENGTH: 2545
<212> TYPE: DNA
<213> ORGANISM: Chlamydia pneumoniae

<400> SEQUENCE: 1

| | | | | | |
|---|---|---|---|---|---|
| ttgcggtgct | gttaacggtg | gagggcagtg | tagtctgagc | agtactcgtt | gctgccgcgc | 60 |
| gcgccaccag | acataatagc | tgacagacta | acagactgtt | cctttccatg | ggtcttttct | 120 |
| gcagtcaccg | tcgtcgacac | gtgtgatcag | atatcgcggc | cgctctagac | cgccatgaca | 180 |
| aaaaaacatt | atgcttgggt | tgtagaaggg | attctcaatc | gtttgcctaa | acagtttttt | 240 |
| gtgaaatgta | gtgttgtcga | ctggaacaca | ttcgttcctt | cagaaacctc | cactacagaa | 300 |
| aaagctgcta | caaacgctat | gaaatacaaa | tactgtgttt | ggcagtggct | cgtcggaaag | 360 |
| catagtcagg | ttccttggat | caatggacag | aaaaagcctc | tatatcttta | tggagctttc | 420 |
| ttaatgaacc | ctttagcaaa | ggctacgaag | actacgttaa | atggaaaaga | aaacctagct | 480 |
| tggtttattg | gaggaacttt | aggggactc | agaaaagctg | gagactggtc | tgccacagta | 540 |
| cgttatgagt | atgtcgaagc | cttgtcagtt | ccagaaatag | atgtttcagg | gattggccgt | 600 |
| ggtaatttat | taaagttttg | gttcgcccaa | gcaattgctg | ctaactatga | tcctaaagag | 660 |
| gctaatagtt | ttacaaatta | taaggatttt | ccgctctat | atatgtatgg | catcacagat | 720 |
| tctctatcat | tcagagctta | tggggcttac | tccaaaccag | caaacgataa | actcggcagt | 780 |
| gattttactt | tccgaaagtt | tgatctaggt | ataatttcag | cgttttaagt | caaattttaa | 840 |
| taaaatcttt | aaaaacaggc | tcgcattaat | tattagtgag | agctttttt | ttatttttta | 900 |
| taataaaact | aaaagatttt | tattattttt | tgagttttta | tggttaatcc | tattggtcca | 960 |
| ggtcctatag | acgaaacaga | acgcacacct | cccgcagatc | tttctgctca | aggattggag | 1020 |
| gcgagtgcag | caaataagag | tgcggaagct | caaagaatag | caggtgcgga | agctaagcct | 1080 |
| aaagaatcta | agaccgattc | tgtagagcga | tggagcatct | tgcgttctgc | agtgaatgct | 1140 |
| ctcatgagtc | tggcagataa | gctgggtatt | gcttctagta | acagctcgtc | ttctactagc | 1200 |
| agatctgcag | acgtggactc | aacgacagcg | accgcaccta | cgcctcctcc | acccacgtct | 1260 |
| gatgattata | agactcaagc | gcaaacagct | tacgatacta | tctttacctc | aacatcacta | 1320 |
| gctgacatac | aggctgcttt | ggtgagcctc | caggatgctg | tcactaatat | aaaggataca | 1380 |
| gcggctactg | atgaggaaac | cgcaatcgct | gcggagtggg | aaactaagaa | tgccgatgca | 1440 |
| attaaagttg | gcgcgcaaat | tacagaatta | gcgaaatatg | cttcggataa | ccaagcgatt | 1500 |
| cttgactctt | taggtaaact | gacttccttc | gacctcttac | agactgctct | tctccaatct | 1560 |
| gtagcaaaca | ataacaaagc | agctgagctt | cttaaagaga | tgcaagataa | cccagtagtc | 1620 |
| ccagggaaaa | cgcctgcaat | tgctcaatct | ttagttgatc | agacagatgc | tacagcgaca | 1680 |
| cagatagaga | aagatggaaa | tgcgattggg | gatgcatatt | ttgcaggaca | gaacgctagt | 1740 |
| ggagctgtag | aaaatgctaa | atctaataac | agtataagca | acatagattc | agctaaagca | 1800 |
| gcaatcgcta | ctgctaagac | acaaatagct | gaagctcaga | aaaagttccc | cgactctcca | 1860 |
| attcttcaag | aagcggaaca | aatggtaata | caggctgaga | agatcttaa | aaatatcaaa | 1920 |
| cctgcagatg | gttctgatgt | tccaaatcca | ggaactacag | ttgaggctc | caagcaacaa | 1980 |
| ggaagtagta | ttggtagtat | tcgtgtttcc | atgctgttag | atgatgctga | aaatgagacc | 2040 |

```
gcttccattt tgatgtctgg gtttcgtcag atgattcaca tgttcaatac ggaaaatcct    2100
gattctcaag ctgcccaaca ggagctcgca gcacaagcta gagcagcgaa agccgctgga    2160
gatgacagtg ctgctgcagc gctggcagat gctcagaaag ctttagaagc ggctctaggt    2220
aaagctgggc aacaacaggg catactcaat gctttgggac agatcgcttc tgctgctgtt    2280
gtgagcgcag gagtcctccc gctgcagcaa gttctatgga tccgagctcg gtaccaagct    2340
tacgtagaac aaaaactcat ctcagaagag gatctgaata gcgccgtcga ccatcatcat    2400
catcatcatt gagtttaaac ggtctccagc ttaagtttaa accgctgatc agcctcgact    2460
gtgccttcta gttgccagcc atctgttgtt tgcccctccc ccgtgccttc cttgaccctg    2520
gaaggtgcca ctcccactgt ccttt                                          2545

<210> SEQ ID NO 2
<211> LENGTH: 651
<212> TYPE: DNA
<213> ORGANISM: Chlamydia pneumoniae

<400> SEQUENCE: 2
atgacaaaaa aacattatgc ttgggttgta gaagggattc tcaatcgttt gcctaaacag      60
ttttttgtga atgtagtgt tgtcgactgg aacacattcg ttccttcaga aacctcccact    120 acagaaaaag ctgctacaaa cgctatgaaa tacaaatact gtgtttggca gtggctcgtc    180
ggaaagcata gtcaggttcc ttggatcaat ggacagaaaa agcctctata tctttatgga    240
gctttcttaa tgaacccttt agcaaaggct acgaagacta cgttaaatgg aaaagaaaac    300
ctagcttggt ttattggagg aactttaggg ggactcagaa agctggaga ctggtctgcc     360 acagtacgtt atgagtatgt cgaagccttg tcagttccag aatagatgt ttcagggatt     420 ggccgtggta atttattaaa gttttggttc gcccaagcaa ttgctgctaa ctatgatcct    480
aaagaggcta atagttttac aaattataaa ggatttccg ctctatatat gtatggcatc     540
acagattctc tatcattcag agcttatggg gcttactcca aaccagcaaa cgataaactc    600
ggcagtgatt ttactttccg aaagtttgat ctaggtataa tttcagcgtt t              651

<210> SEQ ID NO 3
<211> LENGTH: 1470
<212> TYPE: DNA
<213> ORGANISM: Chlamydia pneumoniae

<400> SEQUENCE: 3
atggttaatc ctattggtcc aggtcctata gacgaaacag aacgcacacc tcccgcagat      60
ctttctgctc aaggattgga ggcgagtgca gcaaataaga gtgcggaagc tcaaagaata    120
gcaggtgcgg aagctaagcc taaagaatct aagaccgatt ctgtagagcg atggagcatc    180
ttgcgttctg cagtgaatgc tctcatgagt ctggcagata gctgggtat tgcttctagt     240 aacagctcgt cttctactag cagatctgca gacgtggact caacgacagc gaccgcacct    300
acgcctcctc cacccacgtc tgatgattat aagactcaag cgcaaacagc ttacgatact    360
atctttacct caacatcact agctgacata caggctgctt tggtgagcct ccaggatgct    420
gtcactaata taaggatac agcggctact gatgaggaaa ccgcaatcgc tgcggagtgg     480
gaaactaaga atgccgatgc aattaaagtt ggcgcgcaaa ttacagaatt agcgaaatat    540
gcttcggata ccaagcgat tcttgactct ttaggtaaac tgacttcctt cgacctctta     600
cagactgctc ttctccaatc tgtagcaaac aataacaaag cagctgagct tcttaaagag    660
```

```
atgcaagata acccagtagt cccagggaaa acgcctgcaa ttgctcaatc tttagttgat      720
cagacagatg ctacagcgac acagatagag aaagatggaa atgcgattgg ggatgcatat      780
tttgcaggac agaacgctag tggagctgta gaaaatgcta aatctaataa cagtataagc      840
aacatagatt cagctaaagc agcaatcgct actgctaaga cacaaatagc tgaagctcag      900
aaaaagttcc ccgactctcc aattcttcaa gaagcggaac aaatggtaat acaggctgag      960
aaagatctta aaaatatcaa acctgcagat ggttctgatg ttccaaatcc aggaactaca     1020
gttggaggct ccaagcaaca aggaagtagt attggtagta ttcgtgtttc catgctgtta     1080
gatgatgctg aaaatgagac cgcttccatt ttgatgtctg ggtttcgtca gatgattcac     1140
atgttcaata cggaaaatcc tgattctcaa gctgcccaac aggagctcgc agcacaagct     1200
agagcagcga aagccgctgg agatgacagt gctgctgcag cgctggcaga tgctcagaaa     1260
gctttagaag cggctctagg taaagctggg caacaacagg gcatactcaa tgctttggga     1320
cagatcgctt ctgctgctgt tgtgagcgca ggagtcctcc cgctgcagca agttctatgg     1380
atccgagctc ggtaccaagc ttacgtagaa caaaaactca tctcagaaga ggatctgaat     1440
agcgccgtcg accatcatca tcatcatcat                                      1470

<210> SEQ ID NO 4
<211> LENGTH: 1389
<212> TYPE: DNA
<213> ORGANISM: Chlamydia pneumoniae

<400> SEQUENCE: 4
atggttaatc ctattggtcc aggtcctata gacgaaacag aacgcacacc tcccgcagat       60
ctttctgctc aaggattgga ggcgagtgca gcaaataaga gtgcggaagc tcaaagaata      120
gcaggtgcgg aagctaagcc taaagaatct aagaccgatt ctgtagagcg atggagcatc      180
ttgcgttctg cagtgaatgc tctcatgagt ctggcagata agctgggtat tgcttctagt      240
aacagctcgt cttctactag cagatctgca gacgtggact caacgacagc gaccgcacct      300
acgcctcctc cacccacgtc tgatgattat aagactcaag cgcaaacagc ttacgatact      360
atctttacct caacatcact agctgacata caggctgctt tggtgagcct ccaggatgct      420
gtcactaata taaggatac agcggctact gatgaggaaa ccgcaatcgc tgcggagtgg      480
gaaactaaga atgccgatgc aattaaagtt ggcgcgcaaa ttacagaatt agcgaaatat      540
gcttcggata accaagcgat tcttgactct ttaggtaaac tgacttcctt cgacctctta      600
cagactgctc ttctccaatc tgtagcaaac aataacaaag cagctgagct tcttaaagag      660
atgcaagata acccagtagt cccagggaaa acgcctgcaa ttgctcaatc tttagttgat      720
cagacagatg ctacagcgac acagatagag aaagatggaa atgcgattgg ggatgcatat      780
tttgcaggac agaacgctag tggagctgta gaaaatgcta aatctaataa cagtataagc      840
aacatagatt cagctaaagc agcaatcgct actgctaaga cacaaatagc tgaagctcag      900
aaaaagttcc ccgactctcc aattcttcaa gaagcggaac aaatggtaat acaggctgag      960
aaagatctta aaaatatcaa acctgcagat ggttctgatg ttccaaatcc aggaactaca     1020
gttggaggct ccaagcaaca aggaagtagt attggtagta ttcgtgtttc catgctgtta     1080
gatgatgctg aaaatgagac cgcttccatt ttgatgtctg ggtttcgtca gatgattcac     1140
atgttcaata cggaaaatcc tgattctcaa gctgcccaac aggagctcgc agcacaagct     1200
agagcagcga aagccgctgg agatgacagt gctgctgcag cgctggcaga tgctcagaaa     1260
gctttagaag cggctctagg taaagctggg caacaacagg gcatactcaa tgctttggga     1320
```

```
cagatcgctt ctgctgctgt tgtgagcgca ggagtcctcc cgctgcagca agttctatgg    1380
atccgagct                                                            1389
```

<210> SEQ ID NO 5
<211> LENGTH: 63
<212> TYPE: DNA
<213> ORGANISM: Chlamydia pneumoniae

<400> SEQUENCE: 5

```
cggtaccaag cttacgtaga acaaaaactc atctcagaag aggatctgaa tagcgccgtc      60
gac                                                                   63
```

<210> SEQ ID NO 6
<211> LENGTH: 18
<212> TYPE: DNA
<213> ORGANISM: Chlamydia pneumoniae

<400> SEQUENCE: 6

```
catcatcatc atcatcat                                                   18
```

<210> SEQ ID NO 7
<211> LENGTH: 217
<212> TYPE: PRT
<213> ORGANISM: Chlamydia pneumoniae

<400> SEQUENCE: 7

```
Met Thr Lys Lys His Tyr Ala Trp Val Val Glu Gly Ile Leu Asn Arg
  1               5                  10                  15

Leu Pro Lys Gln Phe Val Lys Cys Ser Val Val Asp Trp Asn Thr
             20                  25                  30

Phe Val Pro Ser Glu Thr Ser Thr Glu Lys Ala Ala Thr Asn Ala
         35                  40                  45

Met Lys Tyr Lys Tyr Cys Val Trp Gln Trp Leu Val Gly Lys His Ser
     50                  55                  60

Gln Val Pro Trp Ile Asn Gly Gln Lys Lys Pro Leu Tyr Leu Tyr Gly
 65                  70                  75                  80

Ala Phe Leu Met Asn Pro Leu Ala Lys Ala Thr Lys Thr Thr Leu Asn
                 85                  90                  95

Gly Lys Glu Asn Leu Ala Trp Phe Ile Gly Gly Thr Leu Gly Gly Leu
            100                 105                 110

Arg Lys Ala Gly Asp Trp Ser Ala Thr Val Arg Tyr Glu Tyr Val Glu
        115                 120                 125

Ala Leu Ser Val Pro Glu Ile Asp Val Ser Gly Ile Gly Arg Gly Asn
    130                 135                 140

Leu Leu Lys Phe Trp Phe Ala Gln Ala Ile Ala Ala Asn Tyr Asp Pro
145                 150                 155                 160

Lys Glu Ala Asn Ser Phe Thr Asn Tyr Lys Gly Phe Ser Ala Leu Tyr
                165                 170                 175

Met Tyr Gly Ile Thr Asp Ser Leu Ser Phe Arg Ala Tyr Gly Ala Tyr
            180                 185                 190

Ser Lys Pro Ala Asn Asp Lys Leu Gly Ser Asp Phe Thr Phe Arg Lys
        195                 200                 205

Phe Asp Leu Gly Ile Ile Ser Ala Phe
    210                 215
```

<210> SEQ ID NO 8

-continued

```
<211> LENGTH: 490
<212> TYPE: PRT
<213> ORGANISM: Chlamydia pneumoniae

<400> SEQUENCE: 8

Met Val Asn Pro Ile Gly Pro Gly Pro Ile Asp Glu Thr Glu Arg Thr
  1               5                  10                  15

Pro Pro Ala Asp Leu Ser Ala Gln Gly Leu Glu Ala Ser Ala Ala Asn
             20                  25                  30

Lys Ser Ala Glu Ala Gln Arg Ile Ala Gly Ala Glu Ala Lys Pro Lys
         35                  40                  45

Glu Ser Lys Thr Asp Ser Val Glu Arg Trp Ser Ile Leu Arg Ser Ala
     50                  55                  60

Val Asn Ala Leu Met Ser Leu Ala Asp Lys Leu Gly Ile Ala Ser Ser
 65                  70                  75                  80

Asn Ser Ser Ser Thr Ser Arg Ser Ala Asp Val Asp Ser Thr Thr
                 85                  90                  95

Ala Thr Ala Pro Thr Pro Pro Pro Thr Ser Asp Asp Tyr Lys Thr
            100                 105                 110

Gln Ala Gln Thr Ala Tyr Asp Thr Ile Phe Thr Ser Thr Ser Leu Ala
        115                 120                 125

Asp Ile Gln Ala Ala Leu Val Ser Leu Gln Asp Ala Val Thr Asn Ile
130                 135                 140

Lys Asp Thr Ala Ala Thr Asp Glu Glu Thr Ala Ile Ala Ala Glu Trp
145                 150                 155                 160

Glu Thr Lys Asn Ala Asp Ala Ile Lys Val Gly Ala Gln Ile Thr Glu
                165                 170                 175

Leu Ala Lys Tyr Ala Ser Asp Asn Gln Ala Ile Leu Asp Ser Leu Gly
            180                 185                 190

Lys Leu Thr Ser Phe Asp Leu Leu Gln Thr Ala Leu Leu Gln Ser Val
        195                 200                 205

Ala Asn Asn Asn Lys Ala Ala Glu Leu Leu Lys Glu Met Gln Asp Asn
210                 215                 220

Pro Val Pro Gly Lys Thr Pro Ala Ile Ala Gln Ser Leu Val Asp
225                 230                 235                 240

Gln Thr Asp Ala Thr Ala Thr Gln Ile Glu Lys Asp Gly Asn Ala Ile
                245                 250                 255

Gly Asp Ala Tyr Phe Ala Gly Gln Asn Ala Ser Gly Ala Val Glu Asn
            260                 265                 270

Ala Lys Ser Asn Asn Ser Ile Ser Asn Ile Asp Ser Ala Lys Ala Ala
        275                 280                 285

Ile Ala Thr Ala Lys Thr Gln Ile Ala Glu Ala Gln Lys Lys Phe Pro
290                 295                 300

Asp Ser Pro Ile Leu Gln Glu Ala Glu Gln Met Val Ile Gln Ala Glu
305                 310                 315                 320

Lys Asp Leu Lys Asn Ile Lys Pro Ala Asp Gly Ser Asp Val Pro Asn
                325                 330                 335

Pro Gly Thr Thr Val Gly Gly Ser Lys Gln Gly Ser Ser Ile Gly
            340                 345                 350

Ser Ile Arg Val Ser Met Leu Leu Asp Asp Ala Glu Asn Glu Thr Ala
        355                 360                 365

Ser Ile Leu Met Ser Gly Phe Arg Gln Met Ile His Met Phe Asn Thr
370                 375                 380

Glu Asn Pro Asp Ser Gln Ala Ala Gln Gln Glu Leu Ala Ala Gln Ala
```

```
            385                390                395                400
Arg Ala Ala Lys Ala Ala Gly Asp Asp Ser Ala Ala Ala Leu Ala
                405                410                415

Asp Ala Gln Lys Ala Leu Glu Ala Ala Leu Gly Lys Ala Gly Gln Gln
                420                425                430

Gln Gly Ile Leu Asn Ala Leu Gly Gln Ile Ala Ser Ala Ala Val Val
                435                440                445

Ser Ala Gly Val Leu Pro Leu Gln Gln Val Leu Trp Ile Arg Ala Arg
        450                455                460

Tyr Gln Ala Tyr Val Glu Gln Lys Leu Ile Ser Glu Glu Asp Leu Asn
465                470                475                480

Ser Ala Val Asp His His His His His His
                485                490

<210> SEQ ID NO 9
<211> LENGTH: 463
<212> TYPE: PRT
<213> ORGANISM: Chlamydia pneumoniae

<400> SEQUENCE: 9

Met Val Asn Pro Ile Gly Pro Gly Pro Ile Asp Glu Thr Glu Arg Thr
  1               5                  10                  15

Pro Pro Ala Asp Leu Ser Ala Gln Gly Leu Glu Ala Ser Ala Ala Asn
                 20                  25                  30

Lys Ser Ala Glu Ala Gln Arg Ile Ala Gly Ala Glu Ala Lys Pro Lys
             35                  40                  45

Glu Ser Lys Thr Asp Ser Val Glu Arg Trp Ser Ile Leu Arg Ser Ala
         50                  55                  60

Val Asn Ala Leu Met Ser Leu Ala Asp Lys Leu Gly Ile Ala Ser Ser
 65                  70                  75                  80

Asn Ser Ser Ser Thr Ser Arg Ser Ala Asp Val Asp Ser Thr Thr
                 85                  90                  95

Ala Thr Ala Pro Thr Pro Pro Pro Thr Ser Asp Asp Tyr Lys Thr
                100                 105                 110

Gln Ala Gln Thr Ala Tyr Asp Thr Ile Phe Thr Ser Thr Ser Leu Ala
            115                 120                 125

Asp Ile Gln Ala Ala Leu Val Ser Leu Gln Asp Ala Val Thr Asn Ile
        130                 135                 140

Lys Asp Thr Ala Ala Thr Asp Glu Glu Thr Ala Ile Ala Ala Glu Trp
145                 150                 155                 160

Glu Thr Lys Asn Ala Asp Ala Ile Lys Val Gly Ala Gln Ile Thr Glu
                165                 170                 175

Leu Ala Lys Tyr Ala Ser Asp Asn Gln Ala Ile Leu Asp Ser Leu Gly
            180                 185                 190

Lys Leu Thr Ser Phe Asp Leu Leu Gln Thr Ala Leu Leu Gln Ser Val
        195                 200                 205

Ala Asn Asn Lys Ala Ala Glu Leu Leu Lys Glu Met Gln Asp Asn
        210                 215                 220

Pro Val Val Pro Gly Lys Thr Pro Ala Ile Ala Gln Ser Leu Val Asp
225                 230                 235                 240

Gln Thr Asp Ala Thr Ala Thr Gln Ile Glu Lys Asp Gly Asn Ala Ile
                245                 250                 255

Gly Asp Ala Tyr Phe Ala Gly Gln Asn Ala Ser Gly Ala Val Glu Asn
            260                 265                 270
```

```
Ala Lys Ser Asn Asn Ser Ile Ser Asn Ile Asp Ser Ala Lys Ala Ala
        275                 280                 285

Ile Ala Thr Ala Lys Thr Gln Ile Ala Glu Ala Gln Lys Lys Phe Pro
    290                 295                 300

Asp Ser Pro Ile Leu Gln Glu Ala Glu Gln Met Val Ile Gln Ala Glu
305                 310                 315                 320

Lys Asp Leu Lys Asn Ile Lys Pro Ala Asp Gly Ser Asp Val Pro Asn
                325                 330                 335

Pro Gly Thr Thr Val Gly Gly Ser Lys Gln Gln Gly Ser Ser Ile Gly
            340                 345                 350

Ser Ile Arg Val Ser Met Leu Asp Asp Ala Glu Asn Glu Thr Ala
        355                 360                 365

Ser Ile Leu Met Ser Gly Phe Arg Gln Met Ile His Met Phe Asn Thr
    370                 375                 380

Glu Asn Pro Asp Ser Gln Ala Ala Gln Gln Glu Leu Ala Ala Gln Ala
385                 390                 395                 400

Arg Ala Ala Lys Ala Ala Gly Asp Asp Ser Ala Ala Ala Ala Leu Ala
                405                 410                 415

Asp Ala Gln Lys Ala Leu Glu Ala Leu Gly Lys Ala Gly Gln Gln
            420                 425                 430

Gln Gly Ile Leu Asn Ala Leu Gly Gln Ile Ala Ser Ala Ala Val Val
        435                 440                 445

Ser Ala Gly Val Leu Pro Leu Gln Gln Val Leu Trp Ile Arg Ala
    450                 455                 460

<210> SEQ ID NO 10
<211> LENGTH: 21
<212> TYPE: PRT
<213> ORGANISM: Chlamydia pneumoniae

<400> SEQUENCE: 10

Arg Tyr Gln Ala Tyr Val Glu Gln Lys Leu Ile Ser Glu Glu Asp Leu
1               5                   10                  15

Asn Ser Ala Val Asp
            20

<210> SEQ ID NO 11
<211> LENGTH: 6
<212> TYPE: PRT
<213> ORGANISM: Chlamydia pneumoniae

<400> SEQUENCE: 11

His His His His His His
1               5

<210> SEQ ID NO 12
<211> LENGTH: 1426
<212> TYPE: DNA
<213> ORGANISM: Chlamydia pneumoniae

<400> SEQUENCE: 12
tgagcagtac tcgttgctgc cgcgcgcgcc accagacata atagctgaca gactaacaga      60
ctgttccttt ccatgggtct tttctgcagt caccgtcgtc gacacgtgtg atcagatatc     120
ccaccatgtt gcctgtaggg aacccttctg atccaagctt attaattgat ggtacaatat     180
gggaaggtgc tgcaggagat ccttgcgatc cttgcgctac ttggtgcgac gctattagct     240
tacgtgctgg attttacgga gactatgttt tcgaccgtat cttaaaagta gatgcaccta     300
```

```
aaacattttc tatgggagcc aagcctactg gatccgctgc tgcaaactat actactgccg    360
tagatagacc taacccggcc tacaataagc atttacacga tgcagagtgg ttcactaatg    420
caggcttcat tgccttaaac atttgggatc gctttgatgt tttctgtact ttaggagctt    480
ctaatggtta cattagagga actctacag cgttcaatct cgttggttta tcggagtta     540
aaggtactac tgtaaatgca atgaactac caaacgtttc tttaagtaac ggagttgttg    600
aactttacac agacacctct ttctcttgga gcgtaggcgc tcgtggagcc ttatgggaat    660
gcggttgtgc aactttggga gctgaattcc aatatgcaca gtccaaacct aaagttgaag    720
aacttaatgt gatctgtaac gtatcgcaat tctctgtaaa caaacccaag ggctataaag    780
gcgttgcttt ccccttgcca acagacgctg gcgtagcaac agctactgga acaaagtctg    840
cgaccatcaa ttatcatgaa tggcaagtag gagcctctct atcttacaga ctaaactctt    900
tagtgccata cattggagta caatggtctc gagcaacttt tgatgctgat aacatccgca    960
ttgctcagcc aaaactacct acagctgttt taaacttaac tgcatggaac ccttcttac    1020
taggaaatgc cacagcattg tctactactg attcgttctc agacttcatg caaattgttt    1080
cctgtcagat caacaagttt aaatctagaa agcttgtgg agttactgta ggagctactt    1140
tagttgatgc tgataaatgg tcacttactg cagaagctcg tttaattaac gagagagctg    1200
ctcacgtatc tggtcagttc agattccggt accaagctta cgtagaacaa aaactcatct    1260
cagaagagga tctgaatagc gccgtcgacc atcatcatca tcatcattga gtttaaacgg    1320
tctccagctt aagtttaaac cgctgatcag cctcgactgt gccttctagt tgccagccat    1380
ctgttgtttg cccctccccc gtgccttcct tgaccctgga aggtgc                  1426
```

<210> SEQ ID NO 13
<211> LENGTH: 1301
<212> TYPE: DNA
<213> ORGANISM: Chlamydia pneumoniae

<400> SEQUENCE: 13

```
atgttgcctg tagggaaccc ttctgatcca agcttattaa ttgatggtac aatatgggaa     60
ggtgctgcag gagatccttg cgatccttgc gctacttggt gcgacgctat tagcttacgt    120
gctggatttt acggagacta tgttttcgac cgtatcttaa aagtagatgc acctaaaaca    180
ttttctatgg gagccaagcc tactggatcc gctgctgcaa actatactac tgccgtagat    240
agacctaacc cggcctacaa taagcattta cacgatgcag agtggttcac taatgcaggc    300
ttcattgcct taaacatttg ggatcgcttt gatgttttct gtactttagg agcttctaat    360
ggttacatta gaggaaactc tacagcgttc aatctcgttg gtttattcgg agttaaaggt    420
actactgtaa atgcaaatga actaccaaac gtttctttaa gtaacggagt tgttgaactt    480
tacacagaca cctcttttct cttggagcgta ggcgctcgtg gagccttatg ggaatgcggt    540
tgtgcaactt gggagctga attccaatat gcacagtcca acctaaagt tgaagaactt    600
aatgtgatct gtaacgtatc gcaattctct gtaaacaaac ccagggcta aaggcgtt     660
gctttcccct tgccaacaga cgctggcgta gcaacagcta ctggaacaaa gtctgcgacc    720
atcaattatc atgaatggca agtaggagcc tctctatctt acagactaaa ctctttagtg    780
ccatacattg gagtacaatg gtctcgagca acttttgatg ctgataacat ccgcattgct    840
cagccaaaac tacctacagc tgttttaaac ttaactgcat ggaacccttc tttactagga    900
aatgccacag cattgtctac tactgattcg ttctcagact tcatgcaaat tgtttcctgt    960
cagatcaaca agtttaaatc tagaaaagct tgtggagtta ctgtaggagc tactttagtt   1020
```

```
gatgctgata aatggtcact tactgcagaa gctcgtttaa ttaacgagag agctgctcac    1080
gtatctggtc agttcagatt ccggtaccaa gcttacgtag aacaaaaact catctcagaa    1140
gaggatctga atagcgccgt cgaccatcat catcatcatc attgagttta aacggtctcc    1200
agcttaagtt taaaccgctg atcagcctcg actgtgcctt ctagttgcca gccatctgtt    1260
gtttgcccct cccccgtgcc ttccttgacc ctggaaggtg c                        1301
```

<210> SEQ ID NO 14
<211> LENGTH: 1101
<212> TYPE: DNA
<213> ORGANISM: Chlamydia pneumoniae

<400> SEQUENCE: 14

```
atgttgcctg tagggaaccc ttctgatcca agcttattaa ttgatggtac aatatgggaa      60
ggtgctgcag gagatccttg cgatccttgc gctacttggt gcgacgctat tagcttacgt     120
gctggatttt acggagacta tgttttcgac cgtatcttaa aagtagatgc acctaaaaca     180
ttttctatgg gagccaagcc tactggatcg gctgctgcaa actatactac tgccgtagat     240
agacctaacc cggcctacaa taagcattta cacgatgcag agtggttcac taatgcaggc     300
ttcattgcct taaacatttg ggatcgcttt gatgttttct gtactttagg agcttctaat     360
ggttacatta gaggaaactc tacagcgttc aatctcgttg gtttattcgg agttaaaggt     420
actactgtaa atgcaaatga actaccaaac gtttctttaa gtaacggagt tgttgaactt     480
tacacagaca cctctttctc ttggagcgta ggcgctcgtg gagccttatg ggaatgcggt     540
tgtgcaactt gggagctga attccaatat gcacagtcca aacctaaagt tgaagaactt     600
aatgtgatct gtaacgtatc gcaattctct gtaaacaaac ccaagggcta taaaggcgtt     660
gctttcccct tgccaacaga cgctggcgta gcaacagcta ctggaacaaa gtctgcgacc     720
atcaattatc atgaatggca gtaggagcc tctctatctt acagactaaa ctcttagtg      780 ccatacattg gagtacaatg gtctcgagca acttttgatg ctgataacat ccgcattgct     840
cagccaaaac tacctacagc tgtttaaaac ttaactgcat ggaaccctc tttactagga    900 aatgccacag cattgtctac tactgattcg ttctcagact tcatgcaaat tgtttcctgt     960
cagatcaaca gttaaaatc tagaaaagct tgtggagtta ctgtaggagc tactttagtt    1020
gatgctgata atggtcact tactgcagaa gctcgtttaa ttaacgagag agctgctcac     1080
gtatctggtc agttcagatt c                                              1101
```

<210> SEQ ID NO 15
<211> LENGTH: 394
<212> TYPE: PRT
<213> ORGANISM: Chlamydia pneumoniae

<400> SEQUENCE: 15

```
Met Leu Pro Val Gly Asn Pro Ser Asp Pro Ser Leu Leu Ile Asp Gly
  1               5                  10                  15

Thr Ile Trp Glu Gly Ala Ala Gly Asp Pro Cys Asp Pro Cys Ala Thr
             20                  25                  30

Trp Cys Asp Ala Ile Ser Leu Arg Ala Gly Phe Tyr Gly Asp Tyr Val
         35                  40                  45

Phe Asp Arg Ile Leu Lys Val Asp Ala Pro Lys Thr Phe Ser Met Gly
     50                  55                  60

Ala Lys Pro Thr Gly Ser Ala Ala Ala Asn Tyr Thr Thr Ala Val Asp
 65                  70                  75                  80
```

-continued

```
Arg Pro Asn Pro Ala Tyr Asn Lys His Leu His Asp Ala Glu Trp Phe
             85                  90                  95

Thr Asn Ala Gly Phe Ile Ala Leu Asn Ile Trp Asp Arg Phe Asp Val
            100                 105                 110

Phe Cys Thr Leu Gly Ala Ser Asn Gly Tyr Ile Arg Gly Asn Ser Thr
        115                 120                 125

Ala Phe Asn Leu Val Gly Leu Phe Gly Val Lys Gly Thr Thr Val Asn
    130                 135                 140

Ala Asn Glu Leu Pro Asn Val Ser Leu Ser Asn Gly Val Val Glu Leu
145                 150                 155                 160

Tyr Thr Asp Thr Ser Phe Ser Trp Ser Val Gly Ala Arg Gly Ala Leu
                165                 170                 175

Trp Glu Cys Gly Cys Ala Thr Leu Gly Ala Glu Phe Gln Tyr Ala Gln
            180                 185                 190

Ser Lys Pro Lys Val Glu Glu Leu Asn Val Ile Cys Asn Val Ser Gln
        195                 200                 205

Phe Ser Val Asn Lys Pro Lys Gly Tyr Lys Gly Val Ala Phe Pro Leu
    210                 215                 220

Pro Thr Asp Ala Gly Val Ala Thr Ala Thr Gly Thr Lys Ser Ala Thr
225                 230                 235                 240

Ile Asn Tyr His Glu Trp Gln Val Gly Ala Ser Leu Ser Tyr Arg Leu
                245                 250                 255

Asn Ser Leu Val Pro Tyr Ile Gly Val Gln Trp Ser Arg Ala Thr Phe
            260                 265                 270

Asp Ala Asp Asn Ile Arg Ile Ala Gln Pro Lys Leu Pro Thr Ala Val
        275                 280                 285

Leu Asn Leu Thr Ala Trp Asn Pro Ser Leu Leu Gly Asn Ala Thr Ala
    290                 295                 300

Leu Ser Thr Thr Asp Ser Phe Ser Asp Phe Met Gln Ile Val Ser Cys
305                 310                 315                 320

Gln Ile Asn Lys Phe Lys Ser Arg Lys Ala Cys Gly Val Thr Val Gly
                325                 330                 335

Ala Thr Leu Val Asp Ala Asp Lys Trp Ser Leu Thr Ala Glu Ala Arg
            340                 345                 350

Leu Ile Asn Glu Arg Ala Ala His Val Ser Gly Gln Phe Arg Phe Arg
        355                 360                 365

Tyr Gln Ala Tyr Val Glu Gln Lys Leu Ile Ser Glu Glu Asp Leu Asn
    370                 375                 380

Ser Ala Val Asp His His His His His His
385                 390

<210> SEQ ID NO 16
<211> LENGTH: 367
<212> TYPE: PRT
<213> ORGANISM: Chlamydia pneumoniae

<400> SEQUENCE: 16

Met Leu Pro Val Gly Asn Pro Ser Asp Pro Ser Leu Leu Ile Asp Gly
  1               5                  10                  15

Thr Ile Trp Glu Gly Ala Ala Gly Asp Pro Cys Asp Pro Cys Ala Thr
             20                  25                  30

Trp Cys Asp Ala Ile Ser Leu Arg Ala Gly Phe Tyr Gly Asp Tyr Val
         35                  40                  45

Phe Asp Arg Ile Leu Lys Val Asp Ala Pro Lys Thr Phe Ser Met Gly
```

```
                50                  55                  60
Ala Lys Pro Thr Gly Ser Ala Ala Asn Tyr Thr Thr Ala Val Asp
 65                  70                  75                  80

Arg Pro Asn Pro Ala Tyr Asn Lys His Leu His Asp Ala Glu Trp Phe
                 85                  90                  95

Thr Asn Ala Gly Phe Ile Ala Leu Asn Ile Trp Asp Arg Phe Asp Val
                100                 105                 110

Phe Cys Thr Leu Gly Ala Ser Asn Gly Tyr Ile Arg Gly Asn Ser Thr
                115                 120                 125

Ala Phe Asn Leu Val Gly Leu Phe Gly Val Lys Gly Thr Thr Val Asn
130                 135                 140

Ala Asn Glu Leu Pro Asn Val Ser Leu Ser Asn Gly Val Val Glu Leu
145                 150                 155                 160

Tyr Thr Asp Thr Ser Phe Ser Trp Ser Val Gly Ala Arg Gly Ala Leu
                165                 170                 175

Trp Glu Cys Gly Cys Ala Thr Leu Gly Ala Glu Phe Gln Tyr Ala Gln
                180                 185                 190

Ser Lys Pro Lys Val Glu Glu Leu Asn Val Ile Cys Asn Val Ser Gln
                195                 200                 205

Phe Ser Val Asn Lys Pro Lys Gly Tyr Lys Gly Val Ala Phe Pro Leu
210                 215                 220

Pro Thr Asp Ala Gly Val Ala Thr Ala Thr Gly Thr Lys Ser Ala Thr
225                 230                 235                 240

Ile Asn Tyr His Glu Trp Gln Val Gly Ala Ser Leu Ser Tyr Arg Leu
                245                 250                 255

Asn Ser Leu Val Pro Tyr Ile Gly Val Gln Trp Ser Arg Ala Thr Phe
                260                 265                 270

Asp Ala Asp Asn Ile Arg Ile Ala Gln Pro Lys Leu Pro Thr Ala Val
                275                 280                 285

Leu Asn Leu Thr Ala Trp Asn Pro Ser Leu Leu Gly Asn Ala Thr Ala
                290                 295                 300

Leu Ser Thr Thr Asp Ser Phe Ser Asp Phe Met Gln Ile Val Ser Cys
305                 310                 315                 320

Gln Ile Asn Lys Phe Lys Ser Arg Lys Ala Cys Gly Val Thr Val Gly
                325                 330                 335

Ala Thr Leu Val Asp Ala Asp Lys Trp Ser Leu Thr Ala Glu Ala Arg
                340                 345                 350

Leu Ile Asn Glu Arg Ala Ala His Val Ser Gly Gln Phe Arg Phe
                355                 360                 365
```

<210> SEQ ID NO 17
<211> LENGTH: 38
<212> TYPE: DNA
<213> ORGANISM: Chlamydia pneumoniae

<400> SEQUENCE: 17
gctctagacc gccatgacaa aaaaacatta tgcttggg                              38

<210> SEQ ID NO 18
<211> LENGTH: 28
<212> TYPE: DNA
<213> ORGANISM: Chlamydia pneumoniae

<400> SEQUENCE: 18
cgggatccat agaacttgct gcagcggg                                         28

```
<210> SEQ ID NO 19
<211> LENGTH: 38
<212> TYPE: DNA
<213> ORGANISM: Chlamydia pneumoniae

<400> SEQUENCE: 19
cccggatatc ccaccatgtt gcctgtaggg aacccttc                           38

<210> SEQ ID NO 20
<211> LENGTH: 31
<212> TYPE: DNA
<213> ORGANISM: Chlamydia pneumoniae

<400> SEQUENCE: 20
ggggtaccgg aatctgaact gaccagatac g                                  31
```

IMMUNOGENIC COMPOSITIONS FOR PROTECTION AGAINST CHLAMYDIAL INFECTION

FIELD OF THE INVENTION

The present invention relates to immunogenic compositions for protection against disease caused by Chlamydia infection in mammals, including humans.

BACKGROUND OF THE INVENTION

Chlamydiae are procaryotes. They exhibit morphologic and structural similarities to gram negative bacteria, including a trilaminar outer membrane, which contains lipopolysaccharide and several membrane proteins Chlamydiae are differentiated from other bacteria by their morphology and by a unique developmental cycle. They are obligate intracellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

Because chlamydiae are small and multiply only within susceptible cells, they were long thought to be viruses. However, they have many characteristics in common with other bacteria: (1) they contain both DNA and RNA, (2) they divide by binary fission, (3) their cell envelopes resemble those of other gram-negative bacteria, (4) they contain ribosomes similar to those of other bacteria, and (5) they are susceptible to various antibiotics. Chlamydiae can be seen in the light microscope, and the genome is about one-third the size of the *Escherichia coli* genome.

Many different strains of chlamydiae have been isolated from birds, man and other mammals, and these strains can be distinguished on the basis of host range, virulence, pathogenesis, and antigenic composition. There is strong homology of DNA within each species, but surprisingly little between species, suggesting longstanding evolutionary separation.

*C. trachomatis* has a high degree of host specificity, being almost completely limited to man, and causes ocular and genitourinary infections of widely varying severity. In contrast, *C. psittaci* strains are rare in man but are found in a wide range of birds and also in wild, domestic, and laboratory mammals, where they multiply in cells of many organs.

*C. pneumoniae* is a common human pathogen, originally described as the TWAR strain of *C. psittaci*, but subsequently recognized to be a new species. *C. pneumoniae* is antigenically, genetically, and morphologically distinct from other Chlamydia species (*C. trachomatis, C. pecorum* and *C. psittaci*). It shows 10% or less DNA sequence homology with either of *C. trachomatis* or *C. psittaci* and so far appears to consist of only a single strain, TWAR.

*C. pneumoniae* is a common cause of community acquired pneumonia, less frequent only than *Streptococcus pneumoniae* and *Mycoplasma pneumoniae* (refs. 1 and 2—Throughout this application, various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure). *C. pneumoniae* can also cause upper respiratory tract symptoms and disease, including bronchitis and sinusitis (refs. 1 to 4). The great majority of the adult population (over 60%) has antibodies to *C. pneumoniae* (ref. 5), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined, but may result from direct contact with secretions, from formites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against chlamydial infections.

In most instances, *C. pneumoniae* infection is mild and without complications, and up to 90% of infections are subacute or unrecognized. Among children in industrialized countries, infections have been thought to be rare up to the age of 5 years, although a recent study has reported that many children in this age group show PCR evidence of infection despite being seronegative, and estimates a prevalence of 17 to 19% in 2 to 4 years old (ref. 6). In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 years. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, C. pneumonia infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (refs. 7 to 11). Moreover, the organisms has been detected in atheromas and fatty streaks of the coronary, carotid, peripheral arteries and aorta (refs. 12 to 16). Viable *C. pneumoniae* has been recovered from the coronary and carotid artery. (refs, 17, 18). Furthermore, it has been shown that *C. pneumoniae* can induce changes of atherosclerosis in a rabbit model (ref. 19). Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbation of asthma in adults, and small-scale studies have shown that prolonged antibiotic treatment was effective at greatly reducing the severity of the disease in some individuals (refs. 20 to 25).

In light of these results, a protective vaccine against disease caused by *C. pneumoniae* infection would be of considerable importance. There is not yet an effective vaccine for human *C. pneumoniae* infection. Nevertheless, studies with *C. trachomatis* and *C. psittaci* indicate that this is an attainable goal. For example, mice which have recovered from a lung infection with *C. trachomatis* are protected from infertility induced by a subsequent vaginal challenge (ref. 26). Similarly, sheep immunized with inactivated *C. psittaci* were protected,from subsequent chlamydial-induced abortions and stillbirths (ref. 27). Protection from chlamydial infections has been associated with Th1 immune responses, particularly the induction of INFγ-producing CD4+ T cells (ref. 28). The adoptive transfer of CD4+ cell lines or clones to nude or SCID mice conferred protection from challenge or cleared chronic disease (refs. 29, 30) and in vivo depletion of CD4+ T cells exacerbated disease post-challenge (refs. 31, 32). However, the presence of sufficiently high titres of neutralizing antibody at mucosal surfaces can also exert a protective effect (ref. 33).

The extent of antigenic variation within the species *C. pneumoniae* is not well characterized. Serovars of *C. trachomatis* are defined on the basis of antigenic variation in major outer membrane proteins (MOMP), but published *C. pneumoniae* MOMP gene sequences show no variation between several diverse isolates of the organism (refs. 34, 35, 36). Regions of the protein known to be conserved in other chlamydial MOMPs are conserved in *C. pneumoniae* (refs. 34, 35). One study has described a strain of *C. pneumoniae* with a MOMP of greater that usual molecular weight, but the gene for this has not been sequenced (ref. 1). Partial sequences of outer membrane protein 2 from nine diverse isolates were also found to be invariant (ref. 17). The genes for HSP60 and HSP70 show little variation from other chlamydial species, as would be expected. The gene encoding a 76 kDa antigen has been cloned from a single strain of *C. pneumoniae*. It has no significant similarity with other known chlamydial genes (ref. 4).

Many antigens recognized by immune sera to *C. pneumoniae* are conserved across all chlamydiae, but 98 kDa, 76 kDa and 54 kDa proteins may be *C. pneumoniae* specific (refs. 2, 4, 37). Immunoblotting of isolates with sera from patients does show variation of blotting patterns between isolates, indicating that serotypes *C. pneumoniae* may exist (refs. 1, 17). However, the results are potentially confounded by the infection status of the patients, since immunoblot profiles of a patient's sera change with time post-infection. An assessment of the number and relative frequency of any serotypes, and the defining antigens, is not yet possible.

Thus, a need remains for effective compositions for preventing and treating Chlamydia infections.

SUMMARY OF THE INVENTION

The present invention provides a novel approach to immunizing against Chlamydial infection based on nucleic acid immunization. It has surprisingly been found that the administration of a combination of nucleotide sequences encoding two different chlamydial proteins provides an enhanced protection efficacy.

Accordingly, in one aspect of the present invention, there is provided an immunogenic composition for in vivo administration to a host for the generation in the host of a protective immune response against Chlamydial infection, comprising a first vector comprising a first nucleotide sequence encoding a major outer membrane protein (MOMP) of a strain of Chlamydia and a first promoter sequence operatively coupled to said first nucleotide sequence for expression of said MOMP in the host; a second vector comprising a second nucleotide sequence encoding a 76 kDa protein of a strain of Chlamydia and a second promoter sequence operatively coupled to said second nucleotide sequence for expression of said 76 kDa protein in the host; and a pharmaceutically-acceptable carrier therefor.

The first nucleotide sequence may encode a MOMP from any strain of Chlamydia, preferably from *C. pneumoniae* but also including *C. trachomatis*. The second nucleotide sequence encoding the MOMP protein of *C. pneumoniae* may have SEQ ID No: 12, 13 or 14 or may encode a MOMP having a SEQ ID No: 1.5 or 16.

The first promoter which is employed may be a cytomegalovirus promoter, although an ther convenient promoter may be employed.

The second nucleotide sequence may encode a 76 kDa protein from any strain of Chlamydia, preferably from *C. pneumoniae* but also including *C. trachomatis*. The second nucleotide sequence encoding the 76 kDa protein of *C. pneumoniae* may have SEQ ID No: 1, 2, 3 or 4. The second nucleotide sequence may encode a 76 kDa protein having a molecular size of about 35 kDa and having SEQ ID No: 7 or may encode a 76 kDa protein having a molecular size of about 60 kDa and having SEQ ID No: 8 or 9.

The second promoter which is employed may be a cytomegalovirus promoter, although any other convenient promoter may be employed.

The first vector preferably comprises a plasmid vector and specifically may be pCAMOMP. Similarly the second vector preferably comprises a plasmid vector and specifically may be pCA76kDa. Most preferably, both the first and second vectors are plasmid vectors and specifically the combination of pCAMOMP and pCA76kDa.

The two vectors are used in an immunogenic composition along with any convenient pharmaceutically-acceptable carrier. As noted above, the uses of the combination of two vectors produces an enhanced protection efficacy in comparison to the individual vectors alone. Accordingly, the first and second vectors preferably are present in the immunogenic composition in amounts such that the individual protective effect of each vector upon administration to the composition to the host is not adversely affected by the other.

The present invention, in a further aspect thereof, provides a method of immunizing a host against disease caused by infection with a strain of Chlamydia, which comprises administering to the host, which may be a human host, an effective amount of an immunogenic composition provided herein. The immunogenic composition preferably is administered intranasally.

BRIEF DESCRIPTION OF THE DRAWINGS

The present invention will be further understood from the following description with reference to the drawings, in which:

FIG. 1 shows the nucleotide sequence of C. pneumoniae 76 kDa gene (SEQ ID No: 1—complete sequence; SEQ ID No: 2-5' encoding region; SEQ ID No: 3-3' encoding region including Myc and His encoding regions; SEQ ID No: 4-3' encoding region excluding Myc and His encoding regions; SEQ ID No: 5—Myc encoding region; SEQ ID No: 6—His encoding region) and the deduced amino acid sequences of two open reading frames of the 76 kDa protein (SEQ ID NO: 7—upstream reading frame; SEQ ID No: 8—downstream reading frame including Myc and His regions; SEQ ID No: 9—downstream reading frame excluding Myc and His regions; SEQ ID No: 10—Myc region; SEQ ID No: 11—His region);

FIG. 2 shows a scheme of construction of plasmid pCA76kDa;

FIG. 3 shows the nucleotide sequence of the C. pneumoniae MOMP gene (SEQ ID No: 12—complete sequence; SEQ ID No: 13—encoding sequence including Myc and His encoding regions; SEQ ID No: 14—encoding sequence excluding Myc and His encoding regions) and the deduced amino acid sequence of the MOMP protein (SEQ ID No: 15—including Myc and His regions; SEQ ID No: 16—excluding Myc and His regions);

FIG. 4 shows a scheme of the construction of plasmid pCAMOMP; and

FIG. 5 illustrates the protective efficacy against *C. pneumoniae* lung challenge in Balb/c mice following DNA immunization with PCAMOMP plus pCA76kDa, in comparison to controls, wherein the individual data points (open diamonds) are shown for each animal, as well as the mean (solid squares) and standard deviation for each group.

GENERAL DESCRIPTION OF INVENTION

As noted above, the present invention is directed to protecting a host against chlamydial infection by administering to the host an immunogenic composition containing two vectors, preferably plasmid vectors, each of which contains nucleotide sequence encoding a different protein of a strain of Chlamydia.

To illustrate the invention, a first plasmid vector was constructed containing the MOMP gene from *C. pneumoniae* and a second plasmid vector was constructed containing the 76 kDa protein gene from *C. pneumoniae*. While the invention is illustrated by the use of such plasmid vectors, other vectors containing such genes may be employed for administration to the host for expression of the encoded proteins in the host. Such other vectors may include live viral vectors, such as adenoviruses, alphaviruses including Semliki Forest virus and poxviruses including avipox and canary pox viruses as well as bacterial vectors, such as Shigella, Salmonella, *Vibrio cholerae*, Lactobacillus, Bacille Bilié de Calmette-Guérin (BCG) and Streptococcus.

One of the vectors employed herein contains a nucleic acid molecule which codes for a Chlamydial protein known in the art as the "76 kDa protein" (ref. 4). The latter terminology is utilized herein to refer to the protein identified in the art. Research has determined that the encoding nucleotide sequence for this protein in fact encodes two opening reading frames, one encoding a protein of approximately 35 kDa in length (SEQ ID No: 7) and the other encoding a protein of approximately 60 kDa in length (SEQ ID No: 9).

It has been found that, if the complete nucleotide sequence (SEQ ID No: 1) is incorporated into a suitable expression vector, then only the 35 kDa protein is expressed. If, however, the nucleotide sequence encoding the 60 kDa protein alone (SEQ ID No: 4) is incorporated into a suitable expression vector, then that protein also can be expressed. Both proteins have been found to be immunogenic and protective with the 35 kDa protein exhibiting a stronger protective effect than the 60 kDa protein (U.S. patent application No. 60/132,270 filed May 3, 1999; U.S. patent application No. 60/1141,276 filed Jun. 30, 1999, assigned to the Assignee hereof and the disclosures of which are incorporated herein by reference).

Any convenient plasmid vector may be used for the MOMP gene and the 76 kDa protein gene, such as the pcDNA3.1 expression vector (Invitrogen, San Diego, Calif., USA) containing the cytomegalovirus promoter. Schemes for construction of the pCA76kDa plasmid vector of 8594 bp size and of the pCAMOMP plasmid vector of 7.6 kb in size, which include downstream DNA sequences coding for Myc and His tags, are shown in FIGS. 2 and 4 respectively and described in detail below.

The respective plasmids are formulated into an immunogenic composition in conjunction with a suitable pharmaceutically-acceptable carrier for administration to a host, such as a human host. The immunogenic composition may be administered in any convenient manner to the host, such as intramuscularly or intranasally, although other routes of administration may be used, as discussed below. The data presented herein and described in detail below demonstrates that DNA immunization with both the *C. pneumoniae* MOMP and 76 kDa protein genes elicits a strong protective immune response. The effect which is obtained is achieved without the use of adjuvant or other stimulation of immune response, such as cardiotoxin, although such materials may be used, if desired, as discussed below. In addition, the use of immunomodulation is not excluded from the scope of the invention. For example, it may be desirable to coadminister DNA that expresses immunoregulator cytokines (ref. 38).

As may be seen from the data below, by utilizing both the MOMP gene and the 76 kDa protein gene, there is obtained a protective immune response which is significantly greater than that achieved using the individual genes alone. The coadministration of the two genes does not result in any interference to the immune response of the individual genes.

There has previously been described in WO 98/02546, assigned to University of Manitoba and the disclosure of which is incorporated herein by reference, the use of the MOMP gene for DNA immunization. The improved results obtained herein using a combination of the MOMP gene and the 76 kDa protein gene demonstrate the use of multiple antigen genes from chlamydiae to augment the level of protective immunity achieved DNA immunization. These results are more encouraging than those obtained using recombinant MOMP protein or synthetic peptides as the immunogen.

Nucleotide sequences, e.g., DNA molecules, can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

It is clearly apparent to one skilled in the art that the various embodiments of the present invention have many applications in the fields of vaccination and treatment of chlamydial infection. A further non-limiting discussion of such uses is further presented below.

1. Vaccine Preparation and Use

Immunogenic compositions, suitable to be used as vaccines, may be prepared from the MOMP gene and the 76 kDa protein gene and vectors as disclosed herein. The vaccine elicits an immune response in a subject which includes the production of anti-MOMP and anti76 kDa protein antibodies. Immunogenic compositions, including vaccines, containing the nucleic acid may be prepared as injectables, in physiologically-acceptable liquid solutions or emulsions for polynucleotide administration.

The nucleic acid may be associated with liposomes, such as lecithin liposomes or other liposomes known in the art, as a nucleic acid liposome (for example, as described in WO 93/24640) or the nucleic acid may be associated with an adjuvant, as described in more detail below. Liposomes comprising cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment.

Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moléculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactide-co-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally, intraperitoneally or intramuscularly, possibly following pretreatment of the injection site with a local anesthetic.

Alternatively, the immunogenic compositions formed according to the present invention, may be formulated and delivered in a manner to evoke an immune response at mucosal surfaces. Thus, the immunogenic composition may be administered to mucosal surfaces by, for example, the ocular, pulminary, nasal or oral (intragastric) routes. Alternatively, other modes of administration including rectal, vaginal or urinary tract as well as suppositories may be desirable. For suppositories, binders and carriers may include, for example, polyalkylene glycols or triglycerides. Oral formulations. may include normally employed incipients, such as, for example, pharmaceutical grades of saccharine, cellulose and magnesium carbonate.

The immunogenic preparations and vaccines are administered in a manner compatible with the dosage formulaton, and in such amount as is therapeutically effective, protective and immunogenic. The quantity to be administered depends on the subject to be treated, including, for example, the capacity of the individual's immune system to synthesize the MOMP and 76 kDa proteins and antibodies thereto, and if needed, to produce a cell-mediated immune response. Precise amounts of active ingredient required to be administered depend on the judgement of the practitioner. However, suitable dosage ranges are readily determinable by one skilled in the art and may be of the order of about 1 µg to about 1 mg of the vectors.

Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity may be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as Quil A derivatives and components thereof, QS 21, calcium phosphate, calcium hydroxide, zinc hydroxide, an octodecyl ester of an amino acid, ISCOPREP, DC-chol, DDBA and polyphosphazene. Advantageous combinations of adjuvants are described in copending U.S. patent application Ser. No. 08/261,194 filed Jun. 16, 1994 and Ser. No. 08/483,856 filed Jun. 7, 1995, assigned to the assignee hereof and the disclosures of which are incorporated herein by reference thereto (WO 95/34308).

In particular embodiments of the present invention, the vectors may be delivered in conjunction with a targeting molecule to target the vectors to selected cells including cells of the immune system.

The vectors may be delivered to the host by a variety of procedures, for example, Tang et al. (ref. 39) disclosed that introduction of gold microprojectiles coated with DNA encoding bovine growth hormone (BGH) into the skin of mice resulted in production of anti-BGH antibodies in the mice, while Furth et al. (ref. 40) showed that a jet injector could be used to transfect skin, muscle, fat and mammary tissues of living animals. See also U.S. Pat. Nos. 4,245,050 and 5,015,580 and WO 94/24263.

EXAMPLES

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient Although specific terms have been employed herein, such terms are intended in a descriptive sense and not for purposes of limitation.

Example 1

This Example illustrates the preparation of a plasmid vector pCA76kDa containing the 76 kDa protein gene.

The 76 kDa protein gene was amplified from Chlamydia pneumoniae (CM1) genomic DNA by polymerase chain reaction (PCR) using a 5' primer (5' GC TCTAGACCGCCATGACAAAAAAACAT TATGCT-TGGG 3') (SEQ ID No: 9) and 3' primer (5' CG GGATCCATAGAACTTGCTGCAGCGGG 3') (SEQ ID No: 10). The 5' primer contains a Xba I restriction site, a ribsome binding site, an initiation codon and a sequence close to the 5' end of the 76 kDa protein coding sequence. The 3' primer includes the sequence encoding the C-terminal sequence of the 76 kDa protein and a Bam HI restriction site. The stop codon was excluded and an additional nucleotide was inserted to obtain an inframe C-terminal fusion with the Histidine tag. The presence of a stop codon at nucleotide 828 of the amplified sequence means that only a partial 76 kDa protein is expressed.

After amplification, the PCR fragment was using QIAquick™ PRC purification kit (Qiagen) and then digested with Xba I and Bam HI and cloned into the pCA-Myc-His eukaryotic expression vector as described in Example 3 below (FIG. 2) with transcription under control of the human CMV promoter.

Example 2

This Example illustrates the preparation of a plasmid vector pCAMOMP containing the MOMP protein gene.

The MOMP protein gene was amplified from Chlamydia pneumoniae (CM1) genomic DNA by polymerase chain reaction (PCR) using a 5' primer (5' CCCG GATATCCCACCATGTTGCCTGTAGG GAACCCTTC 3') (SEQ ID No: 11) and a 3' primer (5' GG GGTACCGGAATCTGAACTGACCAGATACG 3') (SEQ ID No: 12). The 5' primer contains a EcoRV restriction site, a ribosome binding site, an initiation codon and a sequence encoding the N-terminal sequence of the mature MOMP. The 3' primer includes the sequence encoding the C-terminal sequence of the MOMP and a Kpn I restriction site. The DNA sequence encoding the leader peptide was excluded, the stop codon was excluded and an additional nucleotide was inserted to obtain an inframe C-terminal fusion with the Histdine tag.

After amplification, the PCR fragment was purified using QIAquick™ PCR purification kit (Qiagen) and then digested with Eco RV and Kpn I and cloned into the pCA-Myc-His eukaryotic expression vector described in Example 3 (FIG. 4) with transcription under control of the human CMV promoter.

Example 3

This Example illustrates the preparation of the eukaryotic expression vectors pCA76kDa and pCAMOMP.

Plasmid pcDNA3.1 (–) (Invitrogen) was restricted with Spe I and Bam HI to remove the CMV promoter and the remaining vector fragment was isolated. The CMV promoter and intron A from plasmid VR-1012 (Vical) was isolated on a SpeI/Bam HI fragment. The fragments were ligated together to produce plasmid pCA/Myc-His, as seen in FIG. 2.

The Xba I/Bam HI restricted PCR fragment containing the 76 kDa protein gene (Example 1) was ligated into the Xba I and Bam HI restricted plasmid pCA/Myc-His to produce plasmid pCA76kDa (FIG. 2).

The Eco RV/Kpn I restricted PCR fragment containing the MOMP gene (Example 2) was ligated into Eco RV/Kpn I restricted pCA/Myc-His to produce plasmid pCAMOMP (FIG. 4).

The resulting plasmids, pCA76kDa and pCAMOMP, were transferred by electroporation into *E. coli* XL1 blue (Stratagene) which was grown in LB broth containing 50

μg/ml of carbenicillin. The plasmids were isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

Example 4

This Example illustrates the immunization of mice to achieve protection against an intranasal challenge by C. pneumoniae.

It has been previously demonstrated that mice are susceptible to intranasal infection with different isolates of *C. pneumoniae* (ref41). Strain AR-39 (ref. 42) was used in Balb/c mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (5 to 9 per group) were immunized intramuscularly (i.m.) and intranasally (i.n.) with plasmids pCA76kDa and pCAMOMP containing the coding sequences of *C. pneumoniae* 76 kDa and MOMP, respectively, prepared as described in Example 3. Saline or plasmid vectors containing non-protective inserted chlamydial genes, namely pCAI116 and pCAI178,were given to groups of control animals.

The constructs pCAI116 and pCAI178 are identical to pCA76kDa and pCAMOMP except that the nucleotide sequence encoding the partial 76 kDa protein or MOMP is replaced with a *C. pneumoniae* nucleotide sequence encoding, respectively, a possible inclusion membrane protein and a nucleoside 5'-diphosphate phosphotransferase, respectively.

For i.m. immunization, alternate left and right quadriceps were injected with 100 μg of each DNA construct in 50 μl of PBS on three occasions at 0, 3, and 6 weeks. For i.n. immunization, anaesthetized mice aspirated 50 μl of PBS containing 50 μg of each DNA construct on three occasions at 0, 3, and 6 weeks. At week 8, immunized mice were inoculated i.n. with $5\times10^5$ IFU of *C. pneumoniae*, strain AR39, in 100 μl of SPG buffer to test their ability to limit the growth of a sublethal *C. pneumoniae* challenge.

Lungs were taken from mice at day 9 post-challenge and immediately homogenized in SPG buffer (7.5% sucrose, 5 mM glutamate, 12.5 mM phosphate, pH 7.5). The homogenate was stored frozen at −70° C. until assay. Dilutions of the homogenate were assayed for the presence of infectious chlamydia by inoculation onto monolayers of susceptible cells. The inoculum was centrifuged onto the cells at 3000 rpm for 1 hour, then the cells were incubated for three days at 35° C. in the presence of 1 μg/ml cycloheximide. After incubation, the monolayers were fixed with formalin and methanol, then immunoperoxidase stained for the presence of Chlamydial inclusions using convalescent sera from rabbits infected with *C. pneumoniae* and metal-enhanced DAB as a peroxidase substrate.

FIG. 5 and Table 1 contain the results obtained and show that mice immunized i.n. and i m. with both pCA76kDa and pCAMOMP had chlamydial lung titers less than 6700 in 6 of 6 cases, whereas the range of values for control mice with saline were 15,000 to 106,100 IFU/lung in 20 out of 23 cases (mean 49,000) and 12,600 to 80,600 IFU/lung in 11 out of 12 cases (mean 33,500 to 47,000) for mice immunized with the vectors containing non-protective genes (Table 1). The mice immunized with only the pCAMOMP alone showed lung titres in the range of 5800 to 18,700 in 5 out of 6 cases (mean 12,600) and mice immunized with pCA76kDa alone showed similar titres in the range of 6,300 to 18,200 in 5 out of 6 cases (mean 7,400). The increased protection afforded by the combination of the two constructs is surprising in light of other failures due to antigen competition.

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS

| | IMMUNIZING CONSTRUCT | | | | | |
|---|---|---|---|---|---|---|
| MOUSE | Saline Day 9 | pCAI116 Day 9 | pCAI178 Day 9 | pCAMOMP Day 9 | pCA76kDa Day 9 | pCAMOMP + pCA76kDa Day 9 |
| 1 | 1700 | 47700 | 80600 | 5800 | 18200 | 6600 |
| 2 | 36200 | 12600 | 31900 | 30200 | 6300 | 5300 |
| 3 | 106100 | 28600 | 30600 | 9900 | 13400 | 0 |
| 4 | 33500 | 17700 | 6500 | 18700 | 100 | 3300 |
| 5 | 70400 | 77300 | 53000 | 0 | 2400 | 5200 |
| 6 | 48700 | 17600 | 79500 | 11000 | 4000 | 2700 |
| 7 | 600 | | | | | |
| 8 | 19800 | | | | | |
| 9 | 29500 | | | | | |
| 10 | 100000 | | | | | |
| 11 | 15000 | | | | | |
| 12 | 56600 | | | | | |
| 13 | 60300 | | | | | |
| 14 | 88800 | | | | | |
| 15 | 30400 | | | | | |
| 16 | 69300 | | | | | |
| 17 | 47500 | | | | | |
| 18 | 96500 | | | | | |
| 19 | 30200 | | | | | |

TABLE 1-continued

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS
IMMUNIZING CONSTRUCT

| MOUSE | Saline Day 9 | pCAI116 Day 9 | pCAI178 Day 9 | pCAMOMP Day 9 | pCA76kDa Day 9 | pCAMOMP + pCA76kDa Day 9 |
|---|---|---|---|---|---|---|
| 20 | 84800 | | | | | |
| 21 | 3800 | | | | | |
| 22 | 65900 | | | | | |
| 23 | 33000 | | | | | |
| MEAN | 49069.57 | 33583.33 | 47016.67 | 12600 | 7400 | 3850 |
| SD | 32120.48 | 24832.67 | 29524.32 | 10600.19 | 6981.40 | 2363.68 |

SUMMARY OF THE DISCLOSURE

In summary of this disclosure, the present invention provides a novel immunization procedure for obtaining an enhanced protective immune response to Chlamydial infection by employing DNA immunization using nucleotide sequences encoding a MOMP and a 76 kDa protein of a strain of Chlamydia. Modifications are possible within the scope of the invention.

REFERENCES

1. Grayston et al. (1995), Journal of Infectious Diseases 168:1231
2. Campos et al. (1995), Investigation of Ophthalmology and Visual Science 36:1477
3. Grayston et al (1990), Journal of Infectious Diseases 161:618
4. Marrie (1993), Clinical Infectious Diseases. 18:501
5. Wang et al (1986), Chlamydial infections. Cambridge University Press, Cambridge. p.329
6. Norman et al (1998), acta Paediatrica, 87:23–27
7. Saikku et al.(1988), Lancet;ii:983
8. Thom et al. (1992), JAMA 268:68
9. Linnanmaki et al. (1993), Circulation 87:1030
10. Saikku et al. (1992), Annals Internal Medicine 116:273.
11. Melnick et al(1 993), American Journal of Medicine 95:499
12. Shor et al. (1992), South African. Medical Journal 82:158
13. Kuo et al. (1993), Journal of Infectious Diseases 167:841
14. Kuo et al. (1993), Arteriosclerosis and Thrombosis 13:1500
15. Campbell et al (1995), Journal of Infectious Diseases 172:585
16. Chiu et al. Circulation, 1997 (In Press).
17. Ramirez et al (1996) Annals of Internal Medicine 125:979
18. Jackson et al. Abst. K121, p272, 36th ICAAC, 15–18 September 1996, New Orleans.
19. Fong et al (1997) Journal of Clinical Microbiolology 35:48
20. Hahn DL, et al. Evidence for Chlamydia pneumoniae infection in steroid-dependent asthma. Ann Allergy Asthma Immunol. 1998 January; 80(1): 45–49.
21. Hahn DL, et al. Association of Chlamydia pneumoniae IgA antibodies with recently symptomatic asthma. Epidemiol Infect. 1996 December; 117(3): 513–517.
22. Bjomsson E, et al. Serology of chlamydia in relation to asthma and bronchial hyperresponsiveness. Scand J Infect Dis. 1996; 28(1): 63–69.
23. Hahn DL. Treatment of Chlamydia pneumoniae infection in adult asthma: a before-after trial. J Fam Pract. 1995 October: 41(4): 345–351.
24. Allegra L, et al. Acute exacerbations of asthma in adults: role of Chlamydia pneumoniae infection. Eur Respir J. 1994 December; 7(12): 2165–2168.
25. Hahn DL, et al. Association of Chlamydia pneumonlae (strain TWAR) infection with wheezing, asthmatic bronchitis, and adult-onset asthma. JAMA. 1991 Jul. 10; 266(2): 225–230.
26. Pal et al.(1996) Infection and Immunity.64:5341
27. Jones et al. (1995) Vaccine 13:715
28. Igietsemes et al. (1993) Immunology 5:317
29. Igietseme et al (1993) Regional Immunology 5:317
30. Magee et al (1993) Regional Immunology 5: 305
31. Landers et al (1991) Infection & Immunity 59:3774
32. Magee et al (1995) Infection & Immunity 63:516
33. Cotter et al. (1995) Infection and Immunity63:4704
34. Campbell et al (1990) Infection and Immunity 58:93
35. McCafferty et al (1995) Infection and Immunity 63:2387-9.
36. Knudsen et al (1996)Third Meeting of the European Society for Chlamydia Research, Vienna
37. Wiedmann-Al-Ahmad M, et al. Reactions of polyclonal and neutralizing anti-p54 monoclonal antibodies with an isolated, species-specific 54kilodalton protein of Chlamydia pneumoniae. Clin Diagn Lab Immunol. 1997 November; 4(6): 700–704
38. Xiang, 1995, Immunity 2:129–35.
39. Tang et al, Nature 1992; 356:152–154.
40. Furth et al., Vaccine 1994, 12:1503–1509.
41. Yang et al, 1993, Infection & Immunity, vol. 61, pp 2037–40.
42. Chi E. Y., Kuo C. C., Grayston J. T. 1987. Unique ultrastructure in the elementary body of Chlamydia sp strain TWAR. J. Bacteriol 169(8): 3757–63.

We claim:

1. An immunogenic composition, comprising:
   a first plasmid vector comprising:
   a first nucleotide sequence encoding a major outer membrane protein (MOMP) of a strain of *Chlamydia pneumoniae*, said first nucleotide sequence being selected from the group consisting of SEQ ID Nos: 12, 13, and 14 or encoding a MOMP having an amino acid sequence selected from the group consisting of SEQ ID Nos: 15 and 16, and
   a first promoter sequence operatively coupled to said first nucleotide sequence for expression of said MOMP in a host;
   a second plasmid vector comprising:
     a second nucleotide sequence encoding a 76 kDa protein of a strain of *Chlamydia pneumoniae*, said second nucleotide sequence being selected from the group consisting of SEQ ID Nos: 1, 2, 3 and 4, and a second promoter sequence operatively coupled to said second nucleotide sequence for expression of said 76 kDa protein in a host; and
     a pharmaceutically-acceptable carrier therefor.

2. The immunogenic composition of claim 1 wherein the first promoter is a cytomegalovirus promoter.

3. The immunogenic composition of claim 1 wherein said second nucleotide sequence is 76 kDa protein gene sequence encoding a protein having a molecular size of about 35 kDa and having SEQ ID No: 7.

4. The immunogenic composition of claim 1 wherein said second nucleotide sequence is 76 kDa protein gene sequence encoding a protein having a molecular size of about 60 kDa and having SEQ ID No: 8 or 9.

5. The immunogenic composition of claim 1 wherein said second promoter is a cytomegalovirus promoter.

6. The immunogenic composition of claim 1 wherein said first plasmid vector is pCAMOMP and said second plasmid vector is pCA76 kDa.

7. The immunogenic composition of claim 1 wherein said first and second vectors are present in amounts such that upon administration of the composition to the host, the protective effect of the first vector is not adversely affected by the second vector and the protective effect of the second vector is not adversely affected by the first vector.

8. The immunogenic composition of claim 1 wherein said first and second vectors are present in amounts such that an enhanced protective effect is achieved in comparison to the individual vectors alone.

* * * * *